United States Patent
Moix et al.

(10) Patent No.: US 9,459,273 B2
(45) Date of Patent: Oct. 4, 2016

(54) LABORATORY PRODUCT TRANSPORT ELEMENT AND PATH ARRANGEMENT

(75) Inventors: Thomas Moix, Lausanne (CH); Guillaume Ding, Fribourg (CH); Michael Eberhardt, Munich (DE); Martin Mueller, Schliersee-Neuhaus (DE); Sebastian Wiessner, Stephanskirchen (DE); Jurjen Zoethout, La Sarraz (CH)

(73) Assignee: Beckman Coulter, Inc., Brea, CA (US)

( * ) Notice: Subject to any disclaimer, the term of this patent is extended or adjusted under 35 U.S.C. 154(b) by 326 days.

(21) Appl. No.: 14/117,573

(22) PCT Filed: May 11, 2012

(86) PCT No.: PCT/US2012/037527
§ 371 (c)(1),
(2), (4) Date: Apr. 4, 2014

(87) PCT Pub. No.: WO2012/158520
PCT Pub. Date: Nov. 22, 2012

(65) Prior Publication Data
US 2014/0277699 A1    Sep. 18, 2014

Related U.S. Application Data

(60) Provisional application No. 61/486,108, filed on May 13, 2011.

(51) Int. Cl.
G06F 7/00 (2006.01)
G01N 35/04 (2006.01)

(52) U.S. Cl.
CPC ....... *G01N 35/04* (2013.01); *G01N 2035/0422* (2013.01); *G01N 2035/0467* (2013.01); *G01N 2035/0489* (2013.01)

(58) Field of Classification Search
None
See application file for complete search history.

(56) References Cited

U.S. PATENT DOCUMENTS 4,401,189 A    8/1983  Majewski
4,530,056 A    7/1985  MacKinnon et al.
(Continued)

FOREIGN PATENT DOCUMENTS

CN    1234870 A    11/1999
CN    1334453 A     2/2002
(Continued)

OTHER PUBLICATIONS

International Search Report and Written Opinion mailed on Aug. 9, 2012 for PCT Patent Application No. PCT/US2012/037527, 11 pages.
(Continued)

*Primary Examiner* — Yolanda Cumbess
(74) *Attorney, Agent, or Firm* — Kilpatrick Townsend & Stockton LLP

(57) ABSTRACT

The invention concerns a laboratory product transport element for a laboratory transport system with an energy receiver and/or energy accumulator to provide drive power, at least one signal receiver to receive control signals, a control unit to generate drive signals as a function of at least one control signal obtained from the at least one signal receiver, movement devices for independent movement of the laboratory product transport element on a transfer path as a function of the drive signals of the control unit, in which the drive devices are driven by the drive power and at least one holder to hold a laboratory product being transported. The invention also concerns a laboratory transport system with at least one laboratory product transport element according to an embodiment of the invention and a transfer path arrangement. The invention also concerns methods for operation of laboratory transport systems according to an embodiment of the invention.

14 Claims, 26 Drawing Sheets

(56) References Cited

U.S. PATENT DOCUMENTS

| | | | |
|---|---|---|---|
| 4,593,238 A | 6/1986 | Yamamoto | |
| 4,593,239 A | 6/1986 | Yamamoto | |
| 4,703,558 A | 11/1987 | Maekinen | |
| 4,780,817 A | 10/1988 | Lofgren | |
| 4,919,054 A | 4/1990 | Matsuo | |
| 4,947,094 A | 8/1990 | Dyer et al. | |
| 5,075,853 A | 12/1991 | Luke, Jr. | |
| 5,118,191 A | 6/1992 | Hopkins | |
| 5,168,766 A | 12/1992 | Stoffel | |
| 5,179,329 A | 1/1993 | Nishikawa et al. | |
| 5,205,393 A | 4/1993 | Malow et al. | |
| 5,244,055 A | 9/1993 | Shimizu | |
| 5,283,174 A | 2/1994 | Arnold et al. | |
| 5,283,739 A | 2/1994 | Summerville et al. | |
| 5,351,801 A | 10/1994 | Markin et al. | |
| 5,366,896 A | 11/1994 | Margrey et al. | |
| 5,375,898 A | 12/1994 | Ohmori et al. | |
| 5,388,682 A | 2/1995 | Dudley | |
| 5,504,345 A | 4/1996 | Bartunek et al. | |
| 5,582,796 A | 12/1996 | Carey et al. | |
| 5,612,525 A | 3/1997 | Apter et al. | |
| 5,623,415 A | 4/1997 | O'Bryan et al. | |
| 5,652,489 A | 7/1997 | Kawakami | |
| 5,814,008 A | 9/1998 | Chen et al. | |
| 5,814,276 A | 9/1998 | Riggs | |
| 5,814,961 A | 9/1998 | Imahashi | |
| 5,881,781 A | 3/1999 | Bishop | |
| 5,897,090 A | 4/1999 | Smith et al. | |
| 5,966,309 A | 10/1999 | O'Bryan et al. | |
| 6,011,508 A | 1/2000 | Perreault et al. | |
| 6,049,745 A | 4/2000 | Douglas et al. | |
| 6,056,106 A | 5/2000 | van Dyke, Jr. et al. | |
| 6,060,022 A | 5/2000 | Pang et al. | |
| 6,212,448 B1 | 4/2001 | Xydis | |
| 6,368,872 B1 | 4/2002 | Juranas | |
| 6,370,452 B1 | 4/2002 | Pfister | |
| 6,374,989 B1 | 4/2002 | van Dyke, Jr. et al. | |
| 6,377,888 B1 | 4/2002 | Olch | |
| 6,429,016 B1 * | 8/2002 | McNeil | G01N 35/0099 414/222.02 |
| 6,458,324 B1 | 10/2002 | Schinzel | |
| 6,520,313 B1 | 2/2003 | Kaarakainen et al. | |
| 6,586,255 B1 | 7/2003 | Hubert et al. | |
| 6,599,476 B1 | 7/2003 | Watson et al. | |
| 6,629,028 B2 | 9/2003 | Paromtchik et al. | |
| 6,770,883 B2 | 8/2004 | Mc Neal et al. | |
| 6,941,200 B2 | 9/2005 | Sonoyama et al. | |
| 6,993,176 B2 | 1/2006 | Yamagishi et al. | |
| 6,999,847 B2 | 2/2006 | Barry et al. | |
| 7,028,831 B2 | 4/2006 | Veiner | |
| 7,078,698 B2 | 7/2006 | Itoh | |
| 7,174,836 B2 | 2/2007 | Marino et al. | |
| 7,264,111 B2 | 9/2007 | Veiner | |
| 7,269,480 B2 | 9/2007 | Hashimoto et al. | |
| 7,362,258 B2 | 4/2008 | Kawabe et al. | |
| 7,463,948 B2 | 12/2008 | Orita | |
| 7,473,897 B2 | 1/2009 | Braendle et al. | |
| 7,499,581 B2 | 3/2009 | Tribble et al. | |
| 7,688,448 B2 | 3/2010 | Bamberg et al. | |
| 7,746,229 B2 | 6/2010 | Graeter et al. | |
| 7,771,659 B2 | 8/2010 | Ziegler | |
| 7,921,989 B2 | 4/2011 | Itoh | |
| 8,074,578 B2 | 12/2011 | Thornton | |
| 8,322,510 B2 | 12/2012 | Pedrazzini | |
| 8,973,736 B2 | 3/2015 | Johns et al. | |
| 2002/0146347 A1 | 10/2002 | McNeil | |
| 2003/0044319 A1 | 3/2003 | Itoh | |
| 2004/0022682 A1 | 2/2004 | Itoh | |
| 2004/0050836 A1 | 3/2004 | Nesbitt et al. | |
| 2004/0158355 A1 | 8/2004 | Holmqvist et al. | |
| 2005/0163354 A1 | 7/2005 | Ziegler | |
| 2005/0271555 A1 | 12/2005 | Itoh | |
| 2006/0014295 A1 | 1/2006 | Ziegler | |
| 2006/0020370 A1 | 1/2006 | Abramson | |
| 2007/0044676 A1 | 3/2007 | Clark et al. | |
| 2007/0059209 A1 | 3/2007 | Pang et al. | |
| 2007/0100498 A1 | 5/2007 | Matsumoto et al. | |
| 2007/0179690 A1 | 8/2007 | Stewart | |
| 2007/0193859 A1 | 8/2007 | Kyuyoku et al. | |
| 2007/0208440 A1 | 9/2007 | Bliss et al. | |
| 2007/0225901 A1 | 9/2007 | Yamaguchi | |
| 2007/0225906 A1 | 9/2007 | Ikeda | |
| 2008/0167817 A1 | 7/2008 | Hessler et al. | |
| 2008/0297769 A1 | 12/2008 | Bamberg et al. | |
| 2009/0030551 A1 | 1/2009 | Hein et al. | |
| 2009/0324032 A1 | 12/2009 | Chen | |
| 2011/0072913 A1 | 3/2011 | Uhle | |
| 2011/0226584 A1 | 9/2011 | Ek | |
| 2012/0178170 A1 * | 7/2012 | Van Praet | B01L 9/06 436/47 |
| 2014/0202829 A1 | 7/2014 | Eberhardt et al. | |
| 2015/0014125 A1 | 1/2015 | Hecht | |

FOREIGN PATENT DOCUMENTS

| | | |
|---|---|---|
| CN | 1679463 A | 10/2005 |
| CN | 1930478 A | 3/2007 |
| DE | 35 10 797 C2 | 1/1988 |
| DE | 696 33 532 T2 | 2/2006 |
| EP | 0 656 864 B1 | 3/1996 |
| EP | 0 727 665 A2 | 8/1996 |
| EP | 0 680 883 B1 | 12/1998 |
| EP | 0 752 971 B1 | 6/2001 |
| EP | 1 288 758 B1 | 3/2003 |
| EP | 1 326 077 B1 | 9/2004 |
| EP | 1 557 961 A1 | 7/2005 |
| EP | 1 712 971 A2 | 10/2006 |
| EP | 1 712 971 A3 | 10/2006 |
| EP | 1 398 729 B1 | 10/2007 |
| EP | 1 721 671 B1 | 10/2009 |
| EP | 1 731 222 B1 | 3/2010 |
| EP | 2 148 205 B1 | 1/2013 |
| JP | 06-011512 A | 1/1994 |
| JP | 07-049346 A | 2/1995 |
| JP | 07-213586 A | 8/1995 |
| JP | 07-301637 A | 11/1995 |
| JP | 08-285857 A | 11/1996 |
| JP | 08-286749 A | 11/1996 |
| JP | 09-021805 A | 1/1997 |
| JP | 09-080056 A | 3/1997 |
| JP | 09-089902 A | 4/1997 |
| JP | 09-89907 A | 4/1997 |
| JP | 2007-249632 A | 9/2007 |
| WO | 99/28724 A1 | 6/1999 |
| WO | 00/15481 A1 | 3/2000 |
| WO | 00/38046 A1 | 6/2000 |
| WO | 00/67547 A2 | 11/2000 |
| WO | 03/046412 A1 | 6/2003 |
| WO | 2004/013640 A1 | 2/2004 |
| WO | 2006/021052 A1 | 3/2006 |
| WO | 2006/068470 A1 | 6/2006 |
| WO | 2008/043393 A1 | 4/2008 |
| WO | 2008/067847 A1 | 6/2008 |
| WO | 2009/068555 A1 | 6/2009 |
| WO | 2009/097263 A1 | 8/2009 |
| WO | 2010/017528 A2 | 2/2010 |
| WO | 2010/080340 A1 | 7/2010 |
| WO | 2010/081606 A1 | 7/2010 |
| WO | 2011/028166 A1 | 3/2011 |
| WO | 2012/158520 A1 | 11/2012 |
| WO | 2012/185841 A1 | 11/2012 |

OTHER PUBLICATIONS

Caprari, G. et al.; "The autonomous Micro Robot "Alice": a platform for scientific and commercial applications"; *Proceedings of the 1998 International Symposium on Micromechatronics and Human Science*, Nagoya, Japan; Nov. 25-28, 1998; pp. 1-5.

Flexlink®; "TX45E puck handling (mx. 250g),"; located at http://www.flexlink.com/en/offering/conveyor-systems/pallet-and-puck-handling/x45e.jsp; last visited on Jul. 20, 2013; 2 pages.

(56) References Cited

OTHER PUBLICATIONS

Kost, G. J., *Handbook of Clinical Automation, Robotics, and Optimization*; Chapters 1, 10, and 12-14; 1996 by John Wiley & Sons, Inc.; 189 pages total.

Magnemotion; "MagneMover™ LITE,"; located at http://www.magnemotion.com/industrial-automation/magmoverlite.cfm; last visited on Jul. 20, 2013; 3 pages.

Mondada, Francesco et al.; "The e-Puck, a Robot Designed for Education in Engineering", *Proceedings of the 9th Conference on Autonomous Robot Systems and Competitions*, Castelo Branco, Portugal; May 7, 2009; vol. 1; Issue 1; pp. 59-65.

Non-Final Office Action mailed on Apr. 2, 2015 for U.S. Appl. No. 14/117,434, 9 pages.

Notice of Allowance mailed on Jul. 1, 2015 for U.S. Appl. No. 14/117,434, 5 pages.

International Search Report and Written Opinion mailed on Aug. 9, 2012 for PCT Patent Application No. PCT/US2012/037585, 10 pages.

Chinese Office Action mailed on Sep. 11, 2014 for CN Patent Application No. 201280022978.7, with English Translation, 18 pages.

Chinese Office Action mailed on May 27, 2015 for CN Patent Application No. 201280022978.7, with English Translation, 14 pages.

Chinese Office Action mailed on Jul. 1, 2015 for CN Patent Application No. 201280022973.4, with English Translation, 14 pages.

\* cited by examiner

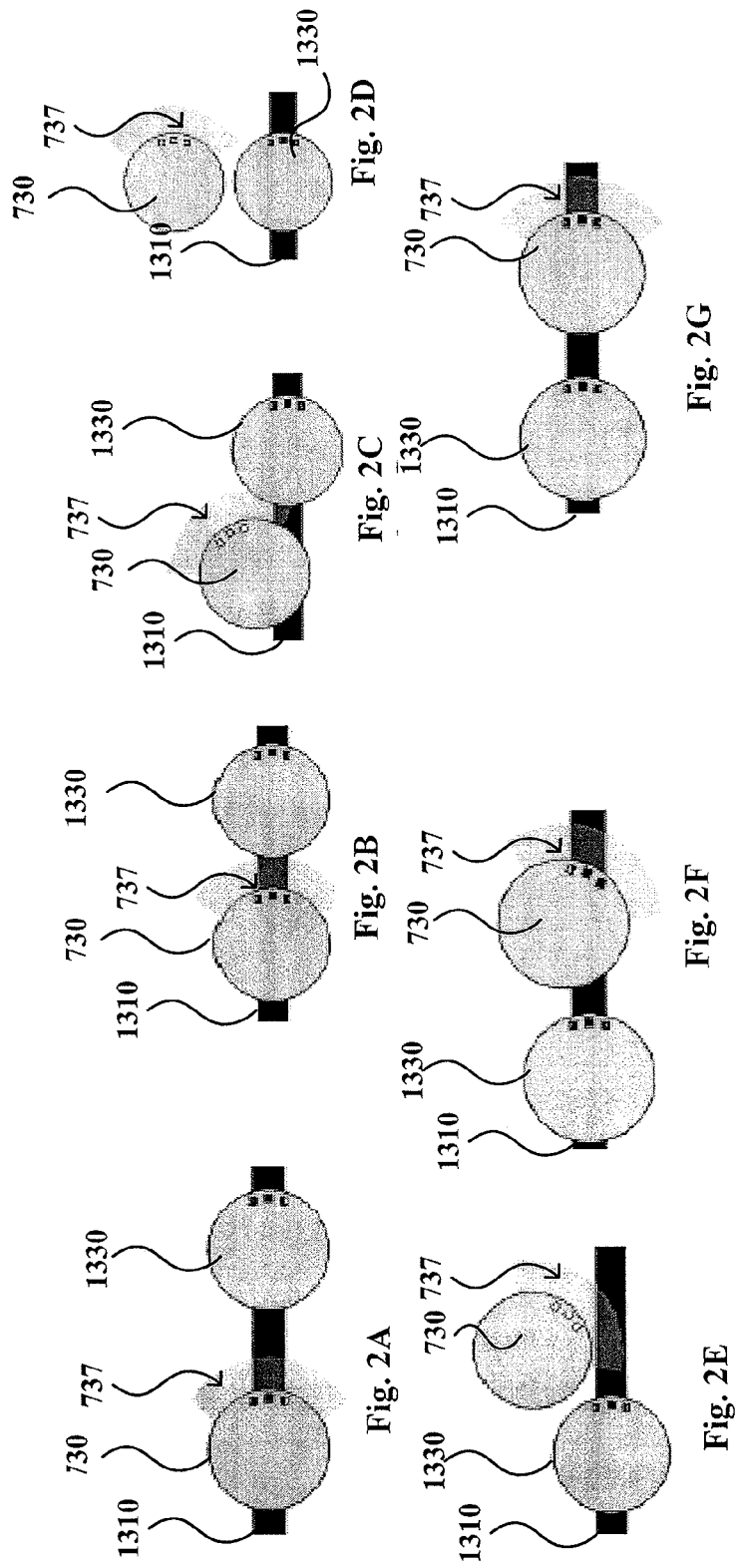

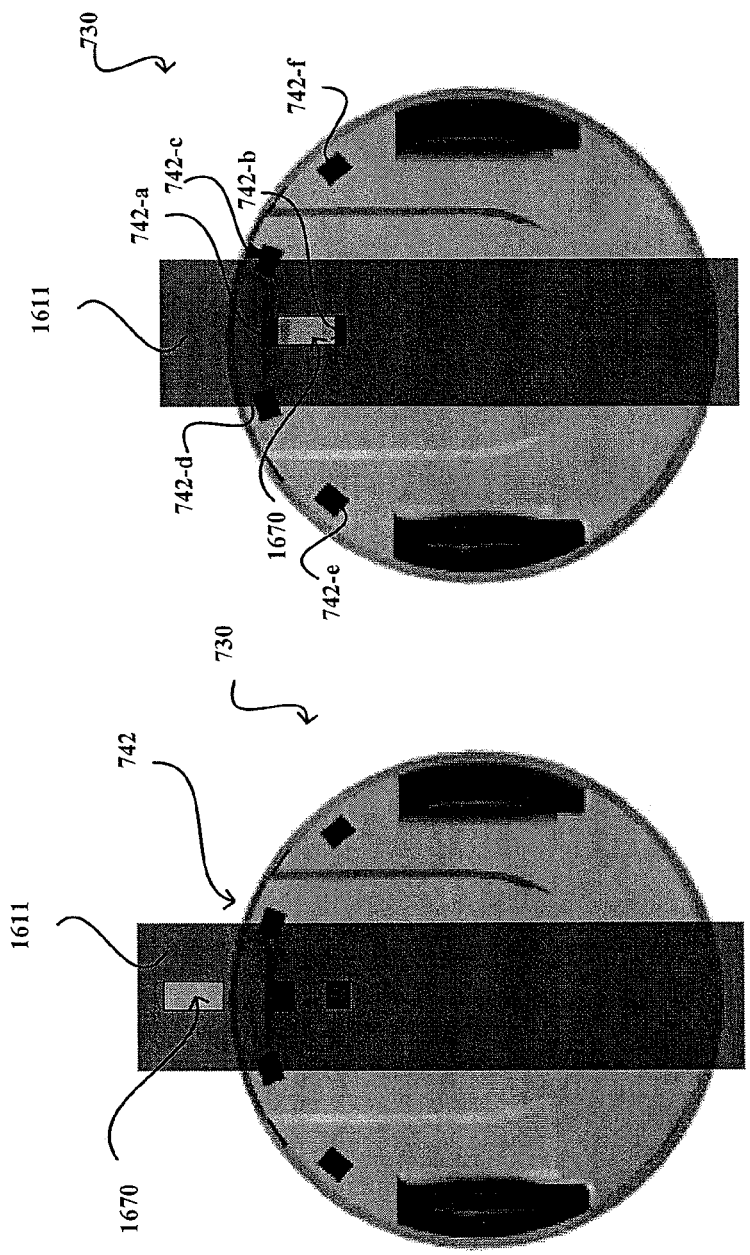

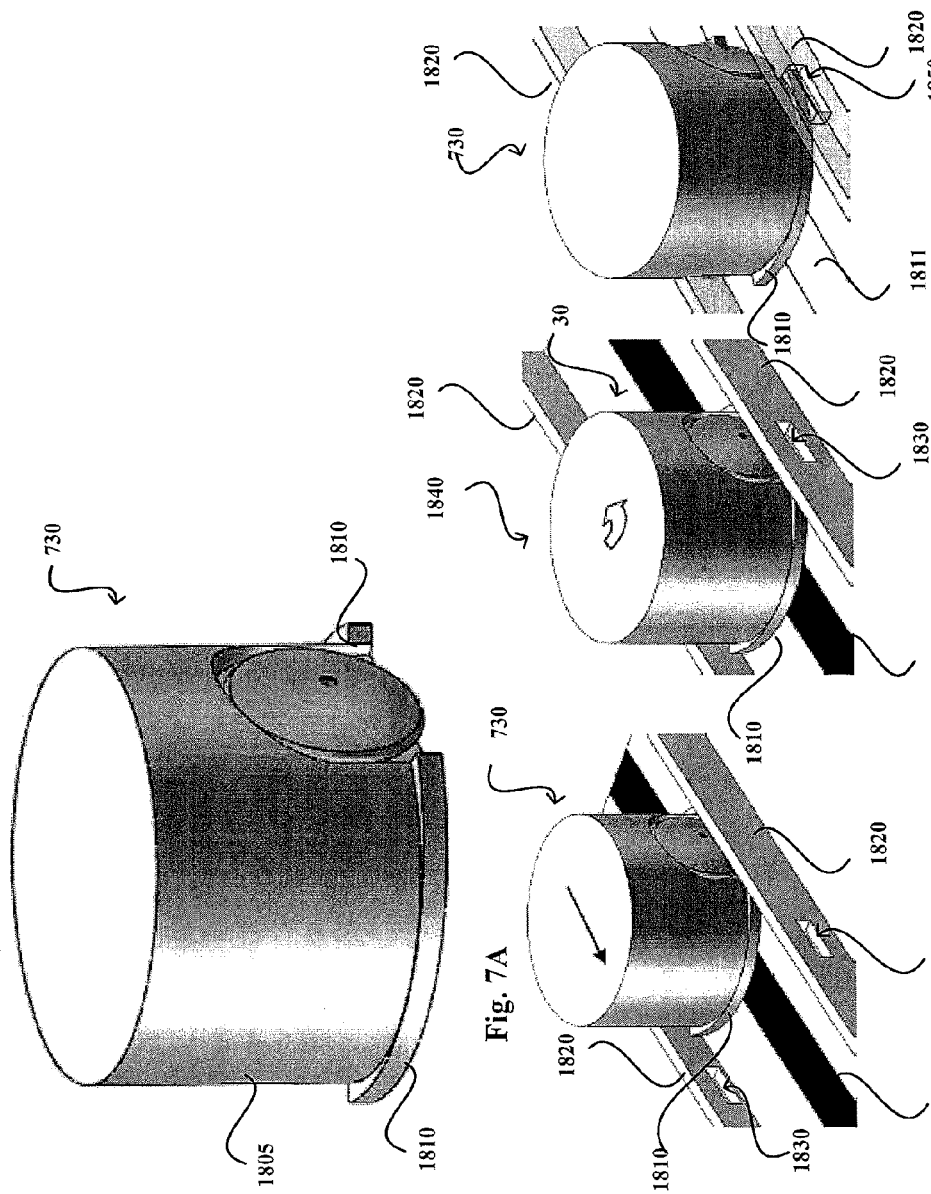

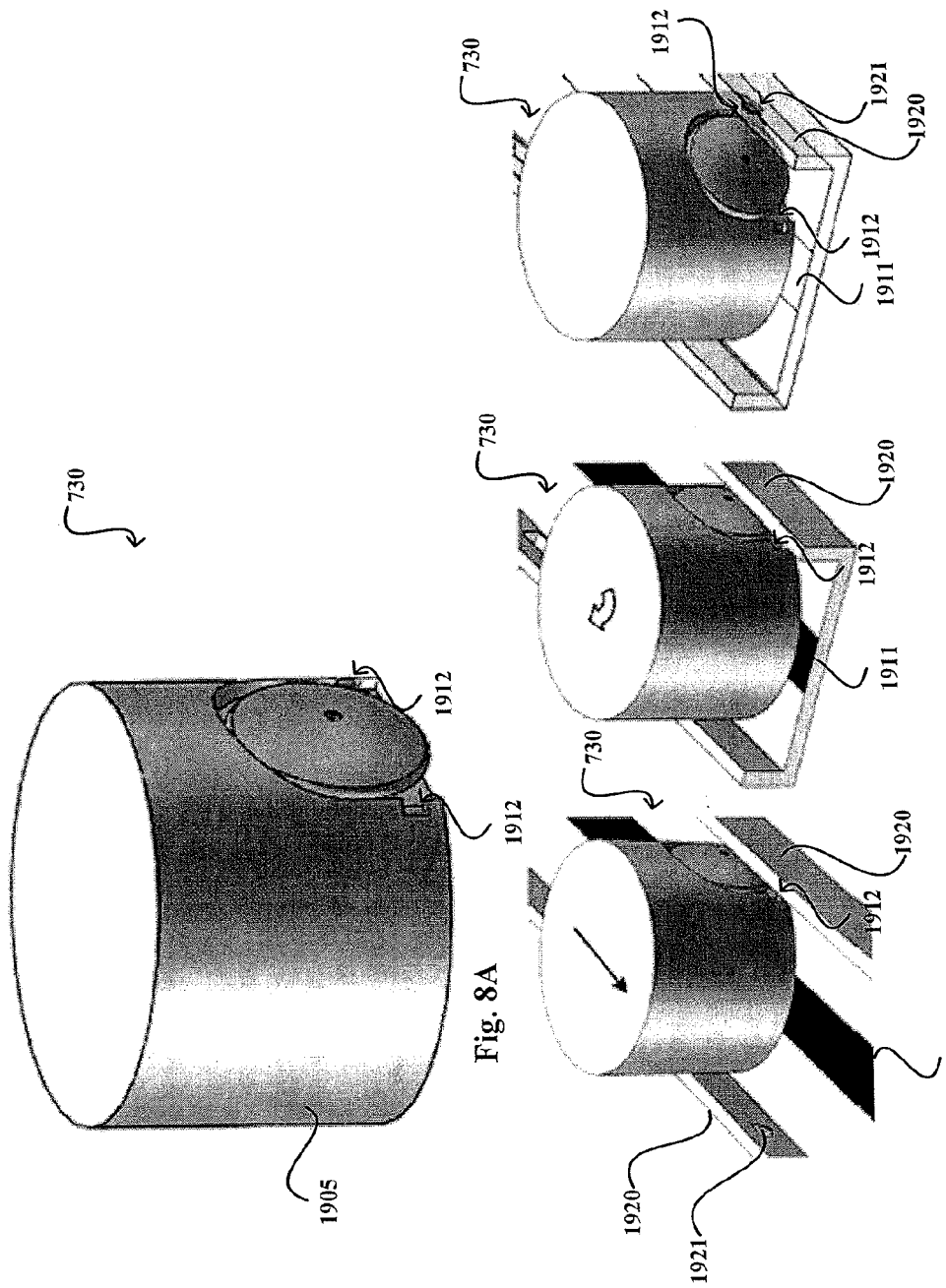

LABORATORY PRODUCT TRANSPORT ELEMENT AND PATH ARRANGEMENT

CROSS-REFERENCE TO RELATED APPLICATIONS

This application is a US National Stage of Entry under §371 of International Application No. PCT/US2012/037527, filed May 11, 2012, which claims the benefit of the filing date of U.S. provisional application No. 61/486,108 filed on May 13, 2011, the disclosures of which are herein incorporated by reference in their entirety for all purposes.

BACKGROUND

Embodiments of the present invention relate to a laboratory transport system that is used in automated medical laboratory in-vitro diagnostic systems for handling patient samples. The transport system of the invention comprises at least one transfer path arrangement and at least one laboratory product transport element which transports laboratory products, such as patient samples, and methods for its operation. Embodiments of the invention also relate to a laboratory product transport element and a transfer path arrangement for a laboratory transport system.

Laboratory transport systems such as gripper systems are used in medical laboratories to transport sample tubes from one processing station to another processing station. Such sample tubes may comprise a sample fluid such as blood, and the sample fluid can be processed for chemical, biological or physical examination.

Individual tubes in the known systems are transported by means of passive laboratory product transport elements ("pucks"), which are moved on an active transport system. By passive it is meant that the pucks cannot move on their own. Active transport systems for moving the pucks from one station to the other include a moving pathway upon which the pucks are positioned or another mechanism for pushing or pulling the puck along a pre-defined path. Examples of moving pathways include chain or belt conveyors. Each possible path is defined by a separate chain or belt conveyor. This produces a complex layout and a high demand for mechanical and electronic components. The drives for the conveyor are often very space-intensive. If the motor used to drive a conveyor, for example, protrudes laterally beyond the actual transport geometry this would preclude the placement of a second conveyor adjacent to the first. Another example of a type of system for moving pucks along a pre-determined path is disclosed in U.S. Pat. Nos. 7,028,831 and 7,264,111. This latter system requires the use of a complicated mechanism for moving the magnets along a pre-determined path. These conventional systems require large complicated mechanisms which take space underneath or adjacent to the puck path. Conveyor drive systems have large areas that are not usable for the transport of pucks at deflections of the chain/belt. It is therefore difficult to implement branching at right angles. In addition, during a change of the puck from a chain or belt to another chain or other belt, a large vibration can occur for the puck, which is not tolerable for many sample materials.

In conventional systems, the mechanical components needed to operate the chain or belt conveyor system or the magnetic transport system are complex. If an element, like a switch, brake or sensor, fails in a conventional system, this can lead to shutdown of the complete transport system, until the disturbance has been eliminated by a service technician.

Finally, changing paths in conventional conveyor systems can be mechanically demanding and expensive. That is, when using a conventional conveyor system, the ability to transport samples according to different protocols is limited, because of the physical constraints provided by such conveyor systems.

The task embodiments of the invention is to provide a laboratory transport system, methods for its operation, a laboratory product transport element and a transfer path arrangement, which permit simple and reliable operation and entail lower design demands. Embodiments of the invention address these and other problems, individually and collectively.

BRIEF SUMMARY

In some embodiments, a laboratory product transport element for a laboratory transport system is provided, where the laboratory product transport element is self-propelled. The laboratory product transport element includes an energy source to furnish drive power. At least one signal receiver is provided to receive control signals. A control unit is provided to generate drive signals as a function of at least one control signal obtained from the at least one receiver. The laboratory product transport element also includes at least one movement device with which the laboratory product transport element can move independently on a transfer path. At least one drive device is provided to drive the movement devices as a function of the drive signals of the control unit. The drive devices may be driven by the drive power. The laboratory product transport element also includes at least one holder to hold a laboratory product to be transported.

Some embodiments include methods for operation of a laboratory transport system in which an objective is stipulated to a laboratory product transport element. The control unit of the laboratory product transport element generates drive signals for the drive devices of the laboratory product transport element by means of a transfer path geometry stored in a memory of the laboratory product transport element and the entered objective.

Some embodiments include methods for operation of a laboratory transport system in which a sequence of drive signals is stored in a memory of a laboratory product transport element. They correspond to a desired path on the at least one transfer path, and the drive devices of the laboratory product transport element move the laboratory product transport element by means of the movement devices and as a function of the drive signals.

Some embodiments include methods for operation of a laboratory transport system in which the laboratory product transport element is controlled in real time.

Some embodiments include methods for operation of a laboratory transport system in which the laboratory product transport element is oriented by means of active or passive orientation features on the transfer path arrangement.

Other embodiments of the invention can relate to predefined laboratory product transport element movement profiles, self-diagnosis, kidnapping protection, fine positioning and lift-off protection, throughput at intersections, energy saving mechanisms, and sample quality protection.

These and other embodiments of the invention are described in further detail below, with reference to the Figures and the Detailed Description.

BRIEF DESCRIPTION OF THE DRAWINGS

A further understanding of the nature and advantages of the different embodiments may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIGS. 2A-2G show an example of a use of a predefined movement profile in accordance with various embodiments.

FIGS. 5A and 5B show an example of fine positioning of a laboratory product transport element in accordance with various embodiments.

FIGS. 7A-7D show an example of lift-off prevention of a laboratory product transport element in accordance with various embodiments.

FIGS. 8A-8D show another example of lift-off prevention of a laboratory product transport element in accordance with various embodiments.

DETAILED DESCRIPTION

Figure 1A:
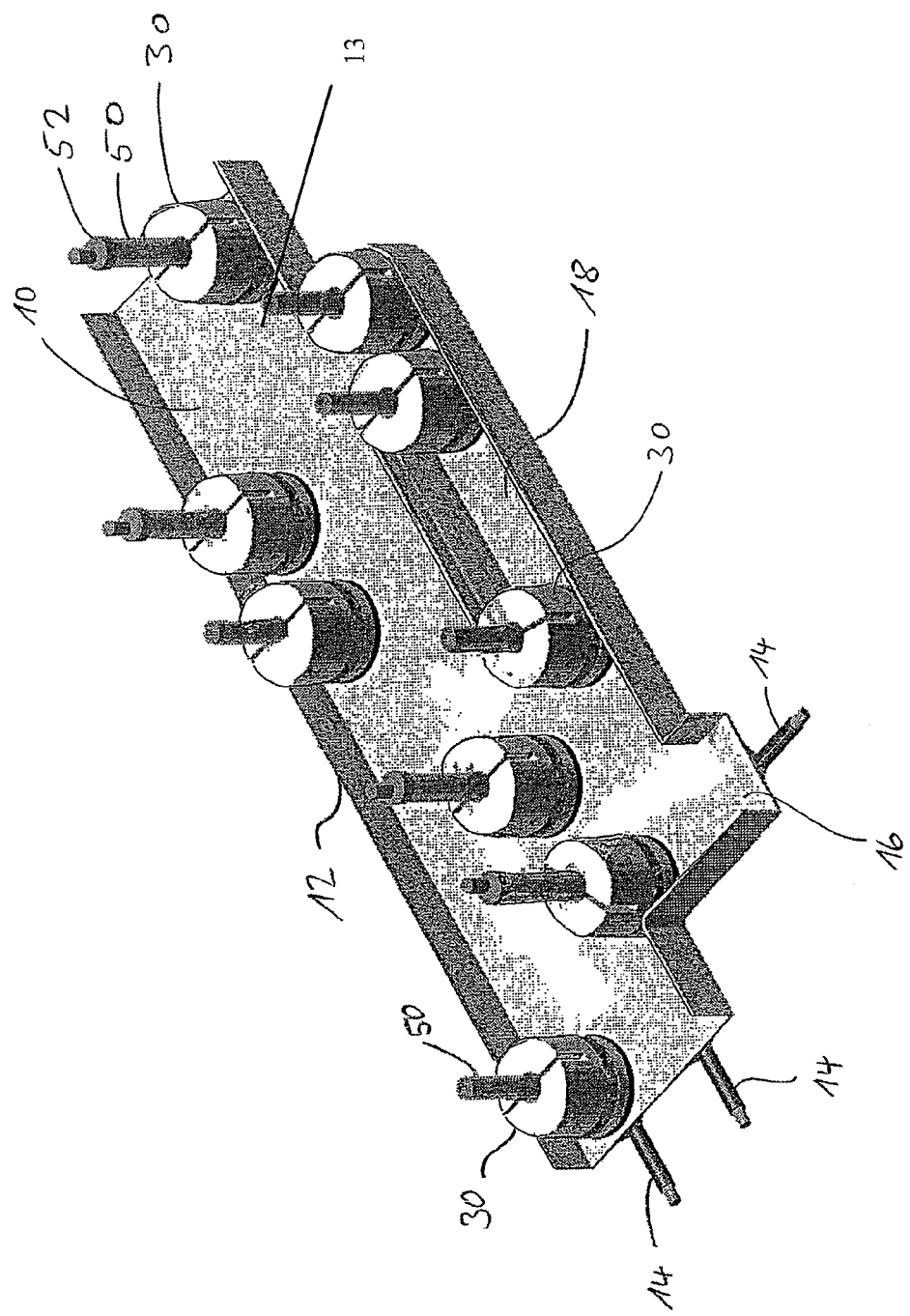
FIG. 1A shows a perspective partial view of a variant of a laboratory transport system in accordance with various embodiments.

The following detailed description may utilize terms as provided below to describe different aspects of different embodiments.

A "laboratory product" may refer to a variety of different containers that may be transported within a laboratory transport system. Examples of such containers include, but are not limited to, a test tube, a sample tube, a sample container, or any container that may be configured to hold a laboratory sample. In addition, a laboratory product may be capped or uncapped in different situations. Also, in some embodiments of the invention, laboratory product may also be pre-centrifuged prior to being transported.

A "laboratory product transport element" may include a variety of different transport elements configured to transport a laboratory product within a laboratory transport system. A laboratory product transport element can transport a laboratory product (e.g., a sample tube) using any suitable mode of transport. Exemplary laboratory product transport elements may include devices which facilitate movement of the element, such as wheels. The transport element can transport one or more laboratory products (e.g., a sample container with a sample in it).

A "laboratory transport system" according to an embodiment of the invention can include at least one laboratory product transport element according to an embodiment of the invention and a transfer path arrangement. A laboratory transport system may include a variety of different subsystems. For example, some laboratory transport systems may include a transfer path arrangement and one or more laboratory product transport elements. Some laboratory transport systems may be active transport systems, while others may be passive transport systems. An active transport systems may include chain or belt conveyors upon which laboratory product transport elements are moved, or transport elements are moved along a path by the magnetic attraction of one or more magnets that are moved along the pre-determined path. Passive transport systems utilize self-propelled transport elements that can avoid the use of chain or belt conveyors or movable magnets, and instead move along transfer surfaces utilizing different movement components that are part of the laboratory product transport element itself.

A "transfer path" may refer to a variety of different surfaces within a laboratory transport system upon which a laboratory product transport element may travel. In some cases, a transfer path may include a smooth surface. A transfer path may be part of a transfer path arrangement that may include one or more transfer paths along with other features in some cases. Suitable examples of transfer paths may include a horizontal web with side limitations (e.g., walls) which can confine the movement of a laboratory product transport element. In some cases, the transfer path may have a marker (e.g., a line) which can be followed by a laboratory product transport element. Transfer paths may head in one or more directions.

A "transfer path arrangement" may include additional features, some of which may be active while others may be passive. A transfer path arrangement may include, but not limited to, barriers, markers, indicators, sensors, transmitters, receivers, electrical conductors, power sources, electromagnetic radiation sources, and/or optical devices.

A "sensor" may refer to a variety of different sensors configured to detect aspects or signals within a laboratory transport system. Sensors may include, but are not limited to: line-following sensors configured to detect line markers within a laboratory transport system; collision sensors configured to detect markers, obstacles, and/or other laboratory product transport elements; and reflective sensors configured to detect one or more position indicators. In some cases, sensors may include RFID readers and/or near-field communication devices.

An "energy source" may refer to a variety of sources of power for components of a laboratory transport system. Energy sources may include sources of drive power for one or more laboratory product transport elements. Energy sources may include an energy receiver and an energy accumulator in some cases. An energy accumulator may include, but is not limited to one or more batteries and/or fuel cells. Energy sources may also include, but are not limited to, voltage sources that may provide energy to a transfer path arrangement.

A "movement device" may refer to a variety of different components that a laboratory product transport element may utilize to move independently along a transfer path. A movement device may include, but is not limited to, a wheel, ball, etc.

A "drive device" may refer to a variety of different components that may drive a movement device. A drive device may receive drive signals from a variety of different sources, including a control unit in some cases. A drive device may include, but is not limited to, different motors such as direct current electric motors.

A "laboratory product transport element" according to an embodiment of the invention can have an energy receiver and/or an energy accumulator to furnish drive power. At least one signal receiver serves to receive control signals, as a function of which a control unit can generate drive signals. Depending on the control signals, drive devices drive movement devices, with which the laboratory product transport element can independently move on a transfer path. The drive devices are operated with the drive power received from the energy receiver and/or stored in an energy accumulator of the laboratory product transport element. Finally, the laboratory product transport element has at least one holder to hold a laboratory product being transported.

An "energy receiver" can include any suitable device that is capable of receiving energy and is capable of providing such energy to a laboratory product transport element. Examples of energy receivers include an induction coil, a photosensitive element (e.g., a photovoltaic cell), a light receiver, a radio signal receiver, etc.

A "signal transmitter" may be any suitable device capable of transmitting a signal from a laboratory product transport element to an external signal receiver. Such signal transmitters can transmit signals using any suitable technology including optical, electrical and magnetic technologies. Examples of signal transmitters can include radio signal transmitters, infrared light transmitters, etc.

A "holder" in a laboratory product transport element may include structures suitable for securely holding a sample container (e.g., a tube) during transportation of the sample container. Exemplary holders may include structures such as housings that may be formed so that they are cooperatively structured with one or more sample containers. In some embodiments, a holder may hold only one laboratory product (e.g., only one sample tube with a sample in it).

The laboratory product transport element can be actively and independently moved on a transfer path with the energy taken from the energy receiver or with the energy stored in the energy accumulator. Control then occurs via signals that are fed from the outside to the signal receiver of the laboratory product transport element and converted by the control unit of the laboratory product transport element. In this way, it is possible that the laboratory product transport element automatically travels to its destination, for example, a processing station or loading or unloading station, and independently takes an ideal route.

A transfer path arrangement that serves to transport such laboratory product transport elements can have a smooth transfer path for movement of a laboratory product transport element or several laboratory product transport elements.

In embodiments of the invention, if a laboratory product transport element is defective, it can be removed from the transfer path and replaced with a new one. A disturbance to the system can therefore always be only locally active and eliminated within a few minutes. By appropriate control or signals, a laboratory product transport element can also be made to independently deviate around a defective stopped laboratory product transport element, so that disturbances can be circumvented.

If different laboratory products are being transported, different laboratory product transport elements could be provided. The different laboratory products can include containers of different sizes, containers with different types of samples, etc.

The laboratory transport system according to an embodiment of the invention is particularly suited for transport of sample tubes in in-vitro diagnostic laboratories, especially for the transport of patient fluid samples between different portions of an in vitro diagnostic system. The laboratory transport system according to an embodiment of the invention, which comprises at least one transfer path and self-driven, intelligent laboratory product transport elements moving on it, represents an inexpensive, highly flexible and extremely space-saving system.

Any suitable drive device can be used in embodiments of the invention. Wheels can be used as a movement device of the laboratory product transport element. In some embodiments, a laboratory product transport element can have two wheels arranged in parallel. A third wheel can be used to steer the laboratory product transport element, which, however, need not necessarily be driven.

In other embodiments, the laboratory product transport element can have movement devices that are individually driven. It is possible to drive one of two parallel wheels more rapidly than the other, so that the laboratory product transport element can move around a curve. By driving two parallel wheels in opposite directions, the laboratory product transport element can rotate around its own axis. This type of drive system, in which the movement device includes at least two individually driven parallel wheels, offers high flexibility. The laboratory product transport element can precisely deliver its transport product to a desired processing station and put it into a desired position.

The laboratory product transport element may also comprise any suitable drive device. For example, an electric motor can be used as a drive device for the wheels.

In one embodiment of the invention, an energy receiver of the laboratory product transport element includes an induction coil, with which energy can be taken from an electromagnetic alternating field (e.g., a high-frequency field).

In one embodiment of the invention, a transfer path arrangement for a laboratory product transport element can include at least one essentially smooth transfer path for movement of a laboratory product transport element or several laboratory product transport elements on it. It may also include at least one electrical conductor configured to generate an electromagnetic alternating field, integrated in or adjacent to at least one transfer path, so that an electromagnetic field generated with the electrical conductor induces an alternating voltage in the induction coil of a laboratory product transport element situated on the transfer path. The transfer path arrangement may further include an alternating voltage source for coupling of an alternating voltage into the at least one electrical conductor.

This type of transfer path arrangement has at least one electrical conductor, with which an electromagnetic alternating field can be generated, and which is integrated in the transfer path or adjacent to the transfer path. An electromagnetic field generated with the electrical conductor is induced in the energy receiver of a laboratory product transport element situated on the transfer path with alternating voltage. In addition, the transfer path arrangement can have an AC source (e.g., a high frequency voltage source), for coupling of an AC signal into the at least one electrical conductor. The high frequency field generated with the at least one electrical conductor of the transfer path arrangement serves as a power supply for the laboratory product transport element, which takes energy from the electromagnetic alternating field by means of the energy receiver via magnetic induction, in order to drive the drive device.

For a system in which the power supply of the laboratory product transport element is derived from an electromagnetic alternating field, electrical conductors can be provided on or in the transfer path along particularly probable paths of the laboratory product transport elements. However, since the laboratory product transport elements move independently, they are not bound to the geometry stipulated by the conductors, as long as the electromagnetic alternating field generator with the conductors at the location of the corresponding laboratory product transport element is sufficiently large for corresponding energy transfer, or the laboratory product transport element has an additional energy accumulator to bridge the areas with an unduly low power supply.

Another embodiment of the laboratory product transport element has at least one photosensitive element as an energy receiver. Through appropriate light units on a transfer path arrangement, power to drive the drive device can be supplied to the laboratory product transport element via the at least one photosensitive element. In some embodiments, the laboratory product transport element has one or more photosensitive elements on the bottom, which can receive power from a light path, which is situated in a surface of a transfer path arrangement according to an embodiment of the invention. The light path can be formed by correspondingly arranged light-emitting diodes.

In a laboratory product transport element embodiment that receives its power from light, light paths can be provided along particularly probable paths that the laboratory product transport elements might take. However, since the laboratory product transport elements move independently, they are not bound to the geometry stipulated by the light paths, as long as sufficient illumination of the photosensitive elements is present or the laboratory product transport element has an energy accumulator to bridge the areas with unduly low illumination.

To bridge the areas with low external power supply, the laboratory product transport element according to an embodiment of the invention has an energy accumulator that serves to provide drive power, if the energy supplied from the outside is not sufficient. This can happen, for example, if, in an embodiment in which the energy is supplied via magnetic induction, the laboratory product transport element is not situated close enough to an electrical conductor of the transfer path arrangement. The electrical conductor may provide the electromagnetic alternating field that furnishes the energy needed to drive the laboratory product transport element. The energy accumulator can also be charged by using power absorbed with an energy receiver.

The laboratory product transport element embodiment that has an additional energy accumulator is advantageous, because the laboratory product transport element has greater independence from the external power supply. Branches, curves or avoidance maneuvers are easier to achieve with the laboratory product transport element.

A charging process can be provided in an embodiment in which the power feed occurs through magnetic induction, such as along straight pieces of the electrical conductor, which are arranged to generate the electromagnetic alternating field on the transfer path arrangement. In an exemplary arrangement in which the power supply occurs via illumination of photosensitive elements of the laboratory product transport elements by means of a light path in the transfer path arrangement, the charging process can also be conducted in the areas that have a straight light path.

Another embodiment of a laboratory product transport element takes energy to drive the drive device exclusively from energy stored in an energy accumulator. This embodiment provides even greater independence to the individual laboratory product transport element. The energy accumulator can be charged at a charging station on the transfer path arrangement, at which a processing station can also be situated. The described energy accumulators, which are either provided in addition to an energy receiver, or exclusively, in order to furnish the drive power, can include a battery or fuel cell.

In embodiments of the invention, signals can be fed to the laboratory product transport element via the at least one signal receiver. This can be, for example, a light receiver (e.g., an infrared light receiver) or a radio signal receiver. In this case, the transfer path arrangement can include a corresponding signal transmitter to transmit signals to the signal receiver of the laboratory product transport element. The signal transmitter, for example, can be a light transmitter (e.g., an infrared light transmitter) or a radio signal transmitter.

The laboratory product transport element can also comprise at least one signal receiver (e.g., a coil). In this embodiment, signals can be fed by means of electromagnetic induction. The coil provided for signal receiving in such an embodiment can also be formed by a coil that serves for energy pickup from an electromagnetic alternating field. In this case, the signal being transmitted can be a frequency-modulated or amplitude-modulated signal, so that it can be distinguished from the alternating field for power supply.

The laboratory product transport element can have any suitable shape. It is desirable if the laboratory product transport element has no sharp corners or edges in its horizontal cross section, so that it is also easy to control along lateral limitations and so that collisions occur as free of vibration as possible. In some embodiments, the laboratory product transport element can have a round horizontal cross section.

To hold the laboratory product being transported, each laboratory product transport element can have at least one holder. When transporting sample tubes, a laboratory product transport element can have a cylindrical recess that is open on the top. The recess may have dimensions that are adapted to the sample tubes being transported. In some cases, a stationary gripper system can easily insert or remove a sample tube into the recess. If the recess is provided roughly in the center of the laboratory product transport element, the sample tube is also optimally secured. Different dimensions of such recesses in different laboratory product transport elements permit transport and handling of different sample tubes. Adjustment of the system to a different sample tube dimension is possible by replacing the corresponding laboratory product transport elements.

Another embodiment of the invention relates to a universal laboratory product transport element, which is suitable for holding differently dimensioned sample tubes or laboratory products. This can be achieved by providing a variable recess in the laboratory product transport element. The recess may be open at the top. The shaped edge of the recess that is open on the top can be made of a flexible material (e.g., foam).

In principle, a laboratory product transport element can have several holders for several different or equivalent laboratory products (e.g., sample tubes with samples). In this way, the laboratory product transport element has greater transport capacity. If, on the other hand, a laboratory product transport element has precisely one holder, then individual transport planning can be used. A laboratory product transport element with only one holder is smaller than a laboratory product transport element with multiple holders.

One laboratory product transport element embodiment that has at least one recess can have a lateral opening such as a side slit. Through this opening, a corresponding optical device or user can easily recognize whether a sample tube is inserted in the corresponding laboratory product transport element. The optical device can also determine how full a tube inside of the recess is. Further, optical investigations of the sample material can also be easily conducted through the opening. Finally, it is possible, through such an opening or slit, to recognize a marking on the lower part of the sample tube being transported and to identify it.

In other embodiments of the invention, laboratory transport systems may implement an optical line following or guiding wire to navigate and move the laboratory product transport elements. Optical line following provides a continuous, uninterrupted line to be read by an optical sensor to determine the direction of movement. Similarly, a guiding wire provides a physical wire for a laboratory product transport element to be tethered to and follow.

In another laboratory transport system embodiment, the transfer path has one or more orientation features, which can be detected by a corresponding sensor of a laboratory product transport element. Such orientation features can be configured passively in the form of barcodes, two dimensional (2D) code, color marks, RFID (radio frequency ID) tags or reflective films. A laboratory product transport element with at least one corresponding sensor (e.g., a scanner) to detect such passive features can be oriented by these orientation features, in order to implement an already received and/or programmed control signal at the correct time. It can also be established, by means of such orientation features, precisely where a laboratory product transport element is situated. For this case, the laboratory product transport element can also have a corresponding signal transmitter in the form of a light transmitter or radio signal transmitter in order to be able to transmit corresponding information.

The orientation features may also be active in nature. Active orientation features may include infrared or radial signal transmitters, which can communicate with corresponding sensors of the laboratory product transport element, when it passes by.

A laboratory product transport element according to an embodiment of the invention may also have a display unit to display information. The display unit allows the laboratory product transport element to provide information as to what it is currently transporting, the transportation path it is currently taking, its status, functional capability, etc. Information provided by the display unit may be generated by the laboratory product transport element during movement, pre-stored in the laboratory product transport element prior to movement, or received from external signals. In some embodiments, the transfer path arrangement of the laboratory transport system can have a recording unit to record information displayed on the display unit.

The display unit of a laboratory product transport element can also show another laboratory product transport element or characteristics thereof. For example, the display unit can show the status or path of an adjacent laboratory product transport element. In this embodiment, the laboratory product transport element can recognize if a laboratory product transport element in front of it or next to it is defective and can take appropriate action pass it or the like. For example, a processor in a first laboratory product transport element can automatically determine the distance to and the position of a second laboratory product transport element in front of it, and can execute code in a memory to cause the first laboratory product transport element to avoid it.

The laboratory product transport element may also comprise at least one signal receiver and/or transmitter, which can also be used for transmitting and receiving data. Such data may include data relating to the sample being transported, data relating to the movement of the laboratory product transport element, data relating to the operational status of the laboratory product transport element, etc. Any data received by the laboratory product transport element may be stored in a memory present in the recording unit of the laboratory product transport element.

Variants of the laboratory product transport element, having a display unit to display information and a corresponding recording unit to record information or corresponding signal receivers and/or transmitters, advantageously allow individual laboratory product transport elements to communicate with each other. This communication can occur directly between various laboratory product transport elements without communication with a station of the laboratory transport system. This can advantageously reduce the number of communication channels in the system.

The laboratory product transport elements according to embodiments of the invention can also communicate with processing stations on a transfer path arrangement of a laboratory transport system. This can be done to provide information about the laboratory product transport element and/or the sample it is transporting to a corresponding processing station. This information can be used to process the transported laboratory product or can be used provide information about the status of the transported laboratory product.

The laboratory product transport element can also have a permanent data memory, protected from power failure, for data storage, as well as a control unit. The control unit can generate drive signals in real time for the drive device. It can receive control signals from the signal receiver in the laboratory product transport element. It is therefore possible to directly control the movement of the laboratory product transport element using external control signals.

The laboratory product transport element may also have a program memory, which can store a sequence of drive signals as computer code. The sequence of drive signals can define a path (e.g., a geometric path) and/or motion (e.g., speed or acceleration) for the laboratory product transport element. The stored drive signals can be programmed into the program memory before actual transport, and these drive signals can be automatically run by the programmed laboratory product transport element. In some cases, the drive signals can be executed after interaction with orientation features on the transfer path, or their execution may be independent of the drive signals. In such embodiments, the signal receiver of the laboratory product transport element can have a wireless programming interface to provide users with the ability to easily program the movements or paths of the laboratory product transport element.

At the beginning of a transport process, a control signal can be provided to the laboratory product transport element via the signal receiver, which corresponds to the objective being controlled. From the geometry of the transfer paths stored in the memory, the control unit then determines the path to be taken, which is automatically traveled by the laboratory product transport element by means of orientation features on the transfer path. This embodiment is therefore capable of independent navigation.

A laboratory product transport element according to an embodiment of the invention can also have one or more Peltier elements for cooling or heating. It can also have heat elements (e.g., designed as resistance wires), so that the transported laboratory product can be kept at a defined temperature or can be temperature-controlled during transport to perform a reaction. In some embodiments, the power supply for temperature control capability can be accomplished via the same power supply system as power supply for providing the drive power of the laboratory product transport element.

The laboratory product transport element according to an embodiment of the invention can also have a position detector, which makes it possible during transport to follow the position. In some embodiments, this can be a position detector that determines a location from a traveled path. For example, position detection device like those used in computer mice can be used in some embodiments of the invention.

In some embodiments, orientation features or barcodes can be provided on a transfer path arrangement for position determination. For example, by using a position detector, which determines the location from the covered path, the position of the laboratory product transport element can be determined after recording of a corresponding orientation feature, until another orientation feature is reached.

Finally, a laboratory product transport element according to an embodiment of the invention can also have a device for position determination that determines the position from direction finding. The direction finding device can use radio direction finding, in which radio signals are evaluated. The radio signals can be generated by radio signal transmitters on the transfer path arrangement.

A laboratory transport system according to an embodiment of the invention can also include at least one transfer path arrangement and at least one laboratory product transport element for movement on the at least one transfer path of the transfer path arrangement. Laboratory products can be transported in the at least one laboratory product transport element. The laboratory transport system is suited for transport of sample containers, such as liquid samples.

The transfer path arrangement of a laboratory transport system according to an embodiment of the invention advantageously includes transfer paths between individual processing stations. At the processing stations, the sample containers or the samples contained in them can be treated and/or investigated.

The laboratory transport system can advantageously include at least one processing station, which includes a loading station or an unloading station to load or unload the laboratory product transport elements. At such stations, sample containers can be inserted into or removed from the laboratory product transport elements.

The laboratory transport system can be suited for devices, in which laboratory products are investigated. In the case of sample containers to be transported, one laboratory transport system according to an embodiment of the invention has at least one processing station for investigation of a sample contained in a sample container. The investigation of the sample can be a physical, chemical or biological examination of the sample.

In a first method according to an embodiment of the invention for operation of a laboratory transport system, an objective can be provided (e.g., programmed into a memory) to a laboratory product transport element. The control unit of the laboratory product transport element generates drive signals for the drive device by using a transfer path geometry stored in a memory of the laboratory product transport element and the entered objective. The drive devices drive the movement devices of the laboratory product transport element as a function of the drive signal so generated, in order to move the laboratory product transport element to the objective. In this embodiment, the laboratory product transport element can automatically navigate to the stipulated objective by means of the stored transfer path geometry.

In another method according an embodiment of the invention for operation of a laboratory transport system, a sequence of drive signals is stored in a memory of a laboratory product transport element. The drive signals can be used to move the laboratory product transport element by means of the movement devices and as a function of the stored drive signals. The drive signals can correspond to a desired path on a transfer path.

In another method according to an embodiment of the invention for operation of a laboratory transport system, the laboratory product transport element can be controlled in real time. It can be controlled by orientation features on the transfer path arrangement. The method according to an embodiment of the invention permits independent and intelligent movement of laboratory product transport elements.

Part of a transfer path arrangement of a laboratory transport system according to an embodiment of the invention is shown in FIG. 1A. A transfer path 10, in particular, with side limitation 12 and a flat horizontal web 13 are visible. In this example, the side limitation 12 can be in the form of a raised wall that can at least partially define the transfer path 10. In this embodiment, there are two raised walls on opposite lateral sides of the flat horizontal web 13, and the walls and the web 13 can define the transfer path 10. Such walls may be of any suitable height depending upon the height of the laboratory product transport element and the sample being carried therein, typically a height of no greater than about 20 mm. Further, the web 13 can be of any suitable lateral dimensions.

Transfer paths according to embodiments of the invention can also have one or more branches that may lead to other areas. For example, the transfer path 10 in FIG. 1 can have a lateral branch 16 that leads to a separation processing station, buffer station, or some other station.

The laboratory transport system can use any suitable numbers or types of devices, which can help guide or move the laboratory product transport elements. As shown in FIG. 1A, electrical conductors 14 (or induction conductors) can be arranged beneath the transfer path 10. The electrical conductors 14 can be electrically coupled to a high frequency voltage source (not shown), so that they can be supplied with high frequency voltage, in order to generate a high frequency electromagnetic alternating field.

Several laboratory product transport elements 30 that transport sample containers 50 (e.g., sample tubes) can move on the transfer path 10. The laboratory product transport elements 30 are described in further below with reference to FIGS. 1B to 1F.

Referring to FIG. 1A, however, the laboratory product transport elements 30 can be transferred to a processing track 18 in defined fashion in a row, in order to be able to carry out, for example, optical investigations of the sample material contained in the sample containers 50.

Electrical conductors 14 can be provided along the particularly probable paths of the laboratory product transport elements 30. However, since the laboratory product transport elements 30 can move independently, they are not bound to the geometry stipulated by the conductors 14. Their movement is not dependent upon the conductors 14, as long as the electromagnetic high frequency field generated with conductors 14 at the location of the laboratory product transport element 30 is sufficient for corresponding energy transmission or the laboratory product transport element 30 has an energy accumulator 44 (see below, FIG. 1E) for bridging.

The sample containers 50 may have any suitable shape or configuration. In some embodiments, the sample containers 50 may be in the form of tubes. In some cases, covers 52 may be on the sample containers, while other sample containers do not have a cover on them and are transported open.

Figure 1B:
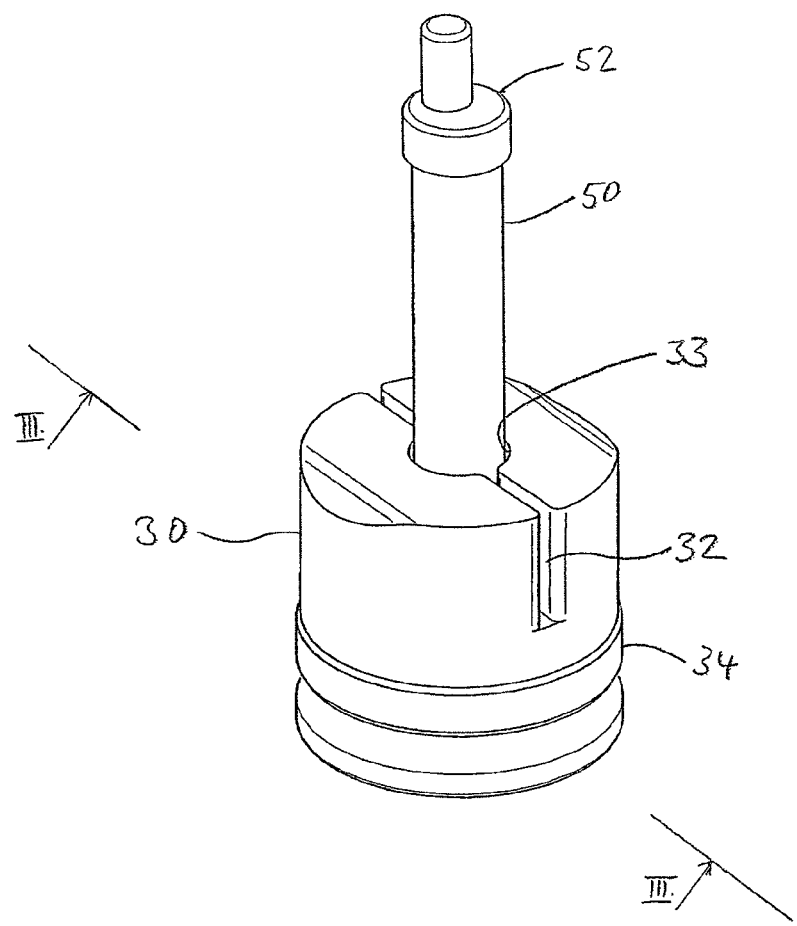
FIG. 1B shows a perspective view of a variant of a laboratory product transport element in accordance with various embodiments.

FIG. 1B shows a side perspective view of a laboratory product transport element 30 according to an embodiment of the invention. The laboratory product transport element 30 comprises a laboratory product transport element housing 31, which may have a cylindrical recess 33 formed at the top of the housing 31, which may also be cylindrical. A sample container 50 with a cover 52 on it may be received in the cylindrical recess 33. A slit 31 may be formed in the side of the housing 31. The slit 31 can permit optical investigation of the sample material contained in the sample container 50, and may be coextensive with the recess 33. In other embodiments, the slit 31 need not be coextensive with the recess 33 and may be formed independent of the recess 33. Furthermore, in other embodiments, the slit 31 can be an aperture that is in some other form (e.g., a circle).

In this example, the laboratory product transport element 30 has a round horizontal cross section and has a rubber strip 34, which serves as an impact protection against the side limitations 12 of the transfer path 10 or other laboratory product transport elements 30.

Figure 1C:
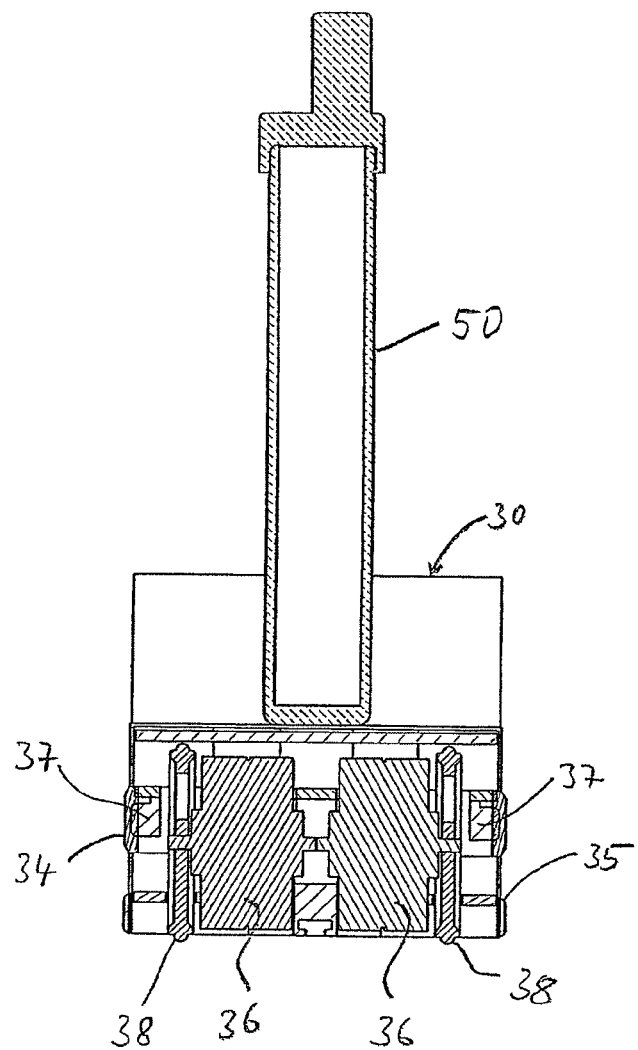
FIG. 1C shows a side sectional view of a variant of the laboratory product transport in accordance with various embodiments.

FIG. 1C shows a side section of the laboratory product transport element 30 in the viewing direction III shown in FIG. 1B. Reference numbers 36 denote electric motors (or drive motors) that drive rubber wheels or rubber-tired wheels 38. Two opposite wheels 38 are provided, which are driven individually by one electric motor 36 each. The wheels 38 may be examples of movement devices.

Figure 3:
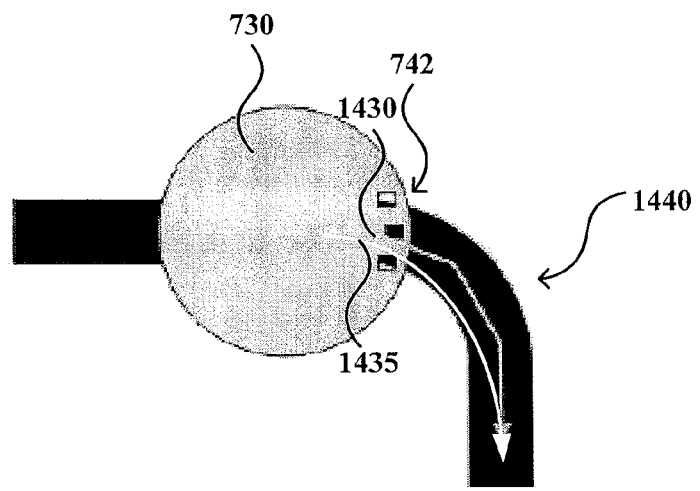
FIG. 3 shows another example of a use of a predefined movement profile in accordance with various embodiments.

A shoulder 35 is shown in FIG. 3, which can cooperate, for example, in transfer path channels configure more narrowly with optionally present side protrusions of side limitations 12 of transfer path 10, in order to hold the laboratory product transport element 30 down, when the sample container 50 is to be pulled out upward from recess 33. The use of shoulder 35 illustrated in FIG. 1C can be described in further detail in the section "Fine Positioning and Lift-Off."

In some embodiments, the laboratory product transport element 30 can have an anchor-like element. The anchor-like element engages in a corresponding mating piece of the transfer path upon entering a processing station, in order to secure the laboratory product transport element 30 during its stay at the processing station.

The laboratory product transport element 30 may also comprise distance sensors 37. In FIG. 3, the distance sensors 37 may include four distance sensors which are arranged behind the rubber strip 34 at angles relative to each other. One preferred embodiment is to have all of the sensors facing forward and at an angular relationship to each other of between 10° and 30°, a more preferred embodiment of 20°.

Figure 1D:
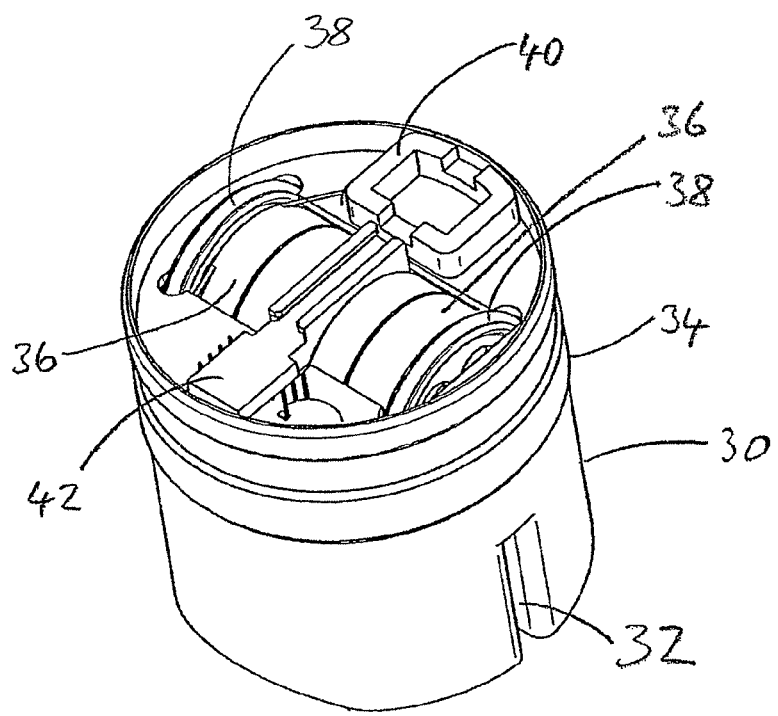
FIG. 1D shows a perspective view of a variant of the laboratory product transport element in accordance with various embodiments from below.
Figure 1E:
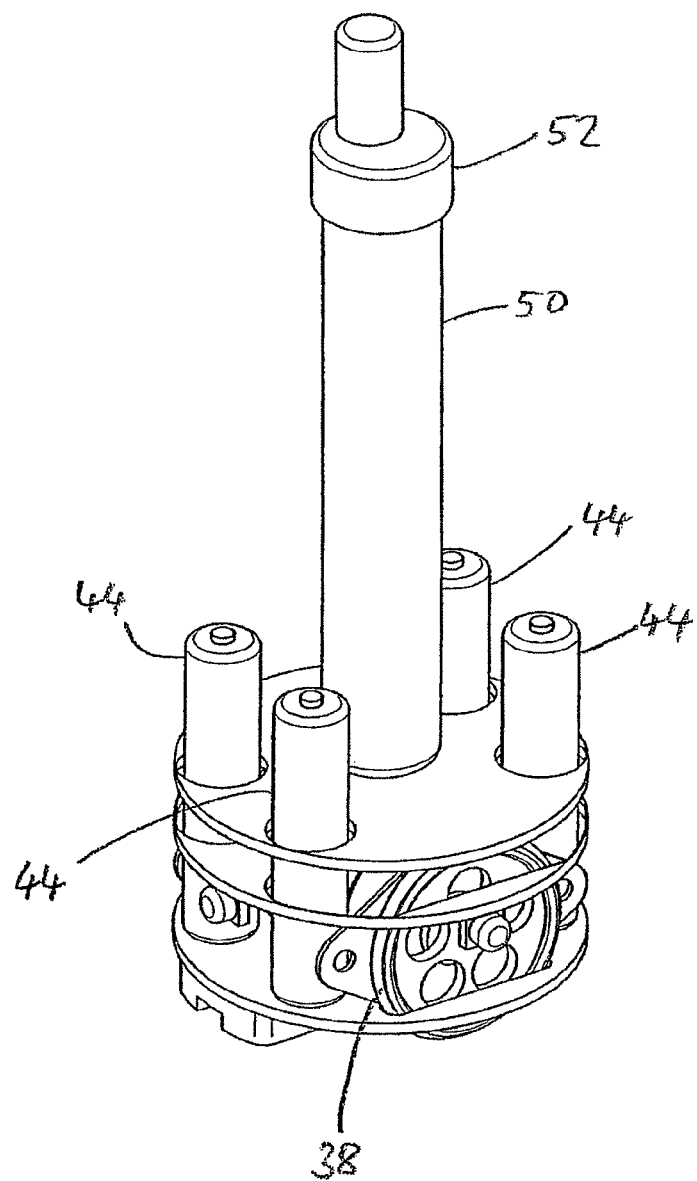
FIG. 1E shows a view of the variant of the laboratory product transport element in accordance with various embodiments without side protection.

FIG. 1D shows a bottom perspective view of the laboratory product transport element 30 according to an embodiment of the invention. The induction coil 40 serves to receive electromagnetic energy from the high frequency fields, which can be generated from electrical conductors 14 beneath the transfer path.

In some embodiments, it is possible that one or more support wheels are provided, in addition to the driven rubber wheels 38, so that the laboratory product transport element 30 rolls on several wheels. However, in other embodiments, no additional wheels are provided, so that the laboratory product transport element, during movement, can lie dragging on one side. This can facilitate curved travel or rotation around its own axis.

In another embodiment of the invention (not shown), the laboratory product transport element 30 is supported on a ball rotatable in all directions, which is arranged offset to the two driven wheels 38, in order to avoid dragging on the transfer path. Such a ball can also be used for position detection, as in a computer mouse.

In the embodiment shown in FIG. 4, reference number 42 denotes a position detector that determines movement of the laboratory product transport element 30, as in a computer mouse that uses laser light. The traveled surface is then illuminated by an incorporated light source and the reflections taken up with an optical sensor, in order to determine movement of the laboratory product transport element 30 from them with corresponding image processing algorithms. The position detector 42 can include a CCD camera and corresponding software, a laser as in a laser mouse, or a ball and sensor as in a ball-type mouse.

FIG. 1D shows the laboratory product transport element 30 without external side protection. That is, a housing can be removed to show the internal elements of the laboratory product transport element 30. As shown in FIG. 5, the laboratory product transport element 30 may include energy accumulators 44 (e.g. batteries). The energy accumulators 44 can serve to store energy in order to drive of the laboratory product transport element 30, when the energy generated by the high frequency field of electrical conductors 14, shown in FIG. 1, and transferred to the induction coil 40, as seen in FIG. 4, might be disabled or too limited to drive the laboratory product transport element 30. This might be the case, for example, in curves or passing zones.

The laboratory product transport element 30 also comprises a control unit (not shown), for example, a corresponding microprocessor that receives signals from signal receivers (also not shown). The signal receivers may include infrared light receivers that cooperate with external infrared light transmitters, in order to receive the control signals. Other examples of signal receives may include radio sensors.

Control signals, however, can also be received via the induction coil 40, as seen in FIG. 4, when corresponding signals are supplied to the electrical conductors 14, as seen in FIG. 1. Such control signals can be discriminated from the high frequency field that furnishes energy by a corresponding frequency or amplitude modulation.

The laboratory product transport elements 30 also may optionally have signal transmitters (not shown) in order to produce information and signals. This permits, for example, precise localization of individual selected laboratory product transport elements 30. The signal transmitters may transmit signals using any suitable frequency and any suitable communications protocol.

Figure 1F:
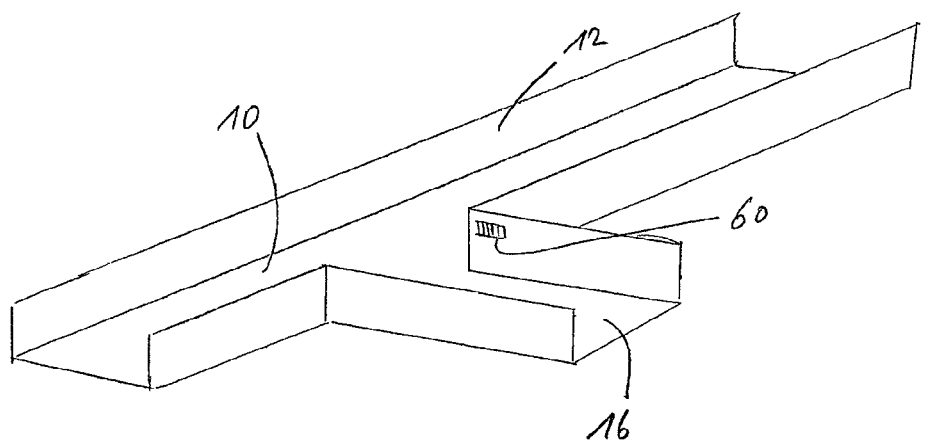
FIG. 1F shows a cutout from a transfer path of a laboratory transport system in accordance with various embodiments.

The laboratory product transport elements 30 can also have a number of sensors, with which position recognition and fine positioning at processing stations, recognition of the travel path limitation or other laboratory product transport elements, or information exchange is possible. For example, clearly identifiable barcodes can be provided on the transfer path 10 shown in FIG. 1, either on the a side limitation 12 or a flat horizontal web 13. The barcodes can be scanned by a laboratory product transport element 30 with one or more sensors configured as scanners, in order to recognize the precise position of a branch or the precise position of a processing station. An example is shown in FIG. 1F by means of a cutout of a transfer path 10. A barcode 60 is situated at a branch 16, which can be recognized and identified by corresponding scanners of a laboratory product transport element. In this way, the laboratory product transport element obtains information concerning its position. A number of such codes could be provided on the transfer path 10, which clearly identify the branches, processing tracks, processing stations or the like.

Other possibilities of such orientation features include 2D codes, color marks, reflection films, transponder systems or infrared light transmitters. Suitable sensors capable of sensing such orientation features can be incorporated into the laboratory product transport elements.

The laboratory product transport element 30 can have a display unit. It can display information as to which path the laboratory product transport element is to take, which laboratory product is being transported, or whether a defect is present. Further, laboratory product transport elements 30, with signal transmitters and receivers, or with display and recording units, can also exchange information with each other either directly via internal communication transmitters, or via a central processor.

In the interior of the laboratory product transport element 30, a permanent data memory, protected from current failure, can be provided, in which data about the transported laboratory product or data about the path being traveled can be entered.

The diameter of the laboratory product transport element 30 depicted in the FIGS. 1A-1E is about 6 cm at a height of about 5.5 cm. The wheels 38 protrude about 1 mm downward from the laboratory product transport element 30. The laboratory product transport elements and features thereof may have other suitable dimensions in other embodiments of the invention.

The laboratory product transport element 30 according to an embodiment of the invention can also have a heating device (not shown). The heating device can keep a sample at a defined temperature during transport or can carry out a defined temperature treatment of the transported sample during the transport. Such a heating device can include, for example, resistance wires which are provided in an appropriate arrangement.

A laboratory transport system according to an embodiment of the invention of the depicted variant can be used, for example, as follows:

Sample containers 50 are inserted into laboratory product transport elements 30 at a loading station by using a stationary gripper system or other container transport system. A target is stipulated to the laboratory product transport element 30 via its signal receiver. The geometry of the actual transfer path 10 can be encoded and entered in a memory of the laboratory product transport element 30. The control unit of the laboratory product transport element 30 can identify the stipulated objective by using data about the transfer path geometry entered in the memory and can independently establish an ideal path to this objective. The locations of orientation features, for example, barcode 60, are also entered in the memory, so that the laboratory product transport element 30 can orient itself during its travel along a path, and to check its current position or correct it, if necessary.

After a start signal is induced in the laboratory product transport element 30, the laboratory product transport element 30 is moved on the pre-defined path established in its memory. If it passes by a barcode 60, at which a direction change is to be made, the barcode 60 recorded with the scanner is used as a signal by the control unit, in order to make a direction change in the desired direction.

If the laboratory product transport element 30, for example, reaches a location, at which a direction change is prescribed, one of the drive motors 36 is stopped or slowed, so that the corresponding wheel 38 stops or rotates more slowly. In this way, the laboratory product transport element 30 travels along a curve.

If the laboratory product transport element 30 reaches its destination (e.g., an unloading station) at which a correspondingly programmed laboratory robot is supposed to remove the transported sample container 50 from the laboratory product transport element 30, the motors 36 are stopped. In order to prevent the laboratory product transport element 30 from being lifted off of the transfer path 10 when the sample container 50 is removed from the recess 33 of the laboratory product transport element 30, the side (i.e. lateral) limitations 12 of the transfer path 10 may have inward-facing protrusions that cooperate with the shoulder 35 on the laboratory product transport element 30. The lateral inward-facing protrusions can prevent the laboratory product transport element 30 from being lifted upward if there is friction between the sample container 50 and the recess 33 of the laboratory product transport element 30.

In some embodiments, the laboratory product transport element 30 brings the sample container 50 to a processing or investigation station, in order to conduct a physical, chemical or biological investigation on the sample. In the case of an optical investigation, the laboratory product transport element 30 reaches a light source on the side with sample container 50. A light source can illuminate the lower area of the sample container 50 through the slit 32 and emitted light from the sample can be detected by a detector arranged opposite it. The detector or electronics associated with the detector can determine the absorption or fluorescence characteristics of the sample. In order for slit 32 to lie precisely opposite the correspondingly arranged light source, the laboratory product transport element can be aligned accordingly. This can be achieved by driving the rubber wheels 38 to rotate in opposite directions. Consequently, the laboratory product transport element 30 rotates around its own axis, until the slit is arranged opposite the corresponding light source for investigation. The slit can also be used to establish the filling level in the sample container 50 or to read out a barcode optionally provided in the lower area of the sample container 50 (e.g. sample tube), which contains information about the transported product.

The laboratory product transport element 30 can also bring the sample container 50 to one or more processing station. Suitable processing stations include an aliquoting station, a station for closing or opening of the sample containers 50, and stations for conducting optical investigations or the like. It should be noted that the laboratory transport system may contain active transport systems which interact with the laboratory product transport element 30 by, for example, the movement of a sample container from the laboratory product transport element 30 onto an active transport system (e.g., a conveyor belt) using a gripper device (not shown).

Alternatively or additionally, it is also possible to configure laboratory product transport elements 30 so that they can be controlled by external controls. For this purpose, a control unit can be used, and configured to convert control signals in real time to drive signals used by the electric motors 36. In this way, it is possible to intervene in the automated laboratory process from the outside and to divert or sort out laboratory product transport elements 30.

It is also possible to fully stipulate the path of the laboratory product transport element 30, for example, by a wireless program interface. The corresponding program can be entered in the data memory of the laboratory product transport element 30. The program data can include information as to at which orientation features (e.g., barcode 60) provided on the side limitation 12 of the transfer path 10 the laboratory product transport element 30 is supposed use to change its direction. In this way, the complete path of the laboratory product transport element 30, with the corresponding sample containers 50, is established and programmed into the laboratory product transport element 30.

If a laboratory product transport element 30 is defective or become inoperable, it can be removed by a user from the transfer path 10 and can optionally be replaced with a new laboratory product transport element 30. If this occurs, the disruption to the system is advantageously short and localized. Further, even if intervention is not possible, the system is not blocked. The other laboratory product transport elements 30 can move around the inoperable laboratory product transport element 30. The other laboratory product transport elements 30 can be prompted by corresponding control signals from a central processor, or via programming of the individual laboratory product transport elements 30 to communicate with other such elements 30. For example, the laboratory product transport elements 30 may have corresponding sensors which can detect the presence of a defective or stationary laboratory product transport element 30 and via programming of the internal control processor move around it.

When they are on the transport path, the individual laboratory product transport elements 30 can also communicate with each other via optical signal transmitters and receivers. This communication can occur directly and need not be conducted via a centrally provided communication site of the laboratory transport system. In this way, a laboratory product transport element with a particularly sensitive sample can inform other laboratory product transport elements that it has priority.

The energy needed to move the laboratory product transport element 30 can be obtained from the electromagnetic field via induction coil 40, which is generated by a high frequency voltage applied to the electrical conductors 14.

The laboratory product transport element 30 need not precisely follow the electrical conductors 14. The interaction only needs to be of sufficient duration so that sufficient energy can be picked up from the electromagnetic field in order to drive the drive motors 36, which drive wheels 38. When this is not possible, the laboratory product transport element 30 can have energy accumulators 44, which supply power to drive motors 36 at such locations of the transfer path 10, in which the electromagnetic field of the electrical conductors 14 is not sufficient. On straight zones, in which the laboratory product transport element 30 can move close to the electrical conductors 14, on the other hand, excess energy from the electromagnetic field can be utilized in order to charge the energy accumulators 44.

Other embodiments of the invention can have photosensitive elements at the bottom of the laboratory product transport element 30. The photosensitive elements can be illuminated by light bands arranged on the transfer path 10. The photosensitive elements can be used to furnish electrical drive power.

It is also possible that the laboratory product transport elements 30 to obtain their drive power completely from energy accumulators 44. The energy accumulators 44 can be charged at corresponding charging stations, which can be at processing stations.

Predefined Movement Profiles

Some embodiments may include methods, systems, and/or devices for controlling the movement of a laboratory product transport element based on predefined movement profiles. These embodiments include methods for a laboratory product transport element to perform movements that can differ from its primary route. These embodiments of the invention can overcome the inflexibility that can come with laboratory product transport elements that can only follow a line on a transport path.

Some embodiments that involve predefined movement profiles may utilize laboratory product transport elements, as shown in FIGS. 2A-2G, such as laboratory product transport elements 30 and/or 730, that may utilize a line following technology such as line following sensors. Embodiments can include the usage of predefined motions, which may be stored in the memory of a laboratory product transport element, that temporarily do not use a line as a guide and/or use the line to fine-adjust movements. An encoder in the laboratory product transport element can provide signals from a drive device to provide feedback for a motion controller.

Embodiments may include predefined movement profiles that provide different functions. For example, a predefined movement profile can allow a laboratory product transport element to leave a lane or line temporarily and follow different possible paths or movements. A predefined movement profile may include information based on one or more speeds, accelerations, distances, and/or directions. In some cases, a predefined movement profile may allow a laboratory product transport element to switch between parallel lines without the need of a physical lane and without stopping and/or interrupting the movement. In another example, a predefined movement profile may allow a laboratory product transport element to perform a queue jumping action, such as entering a waiting queue not at the end of the queue but rather close to a functional spot. This may be especially applicable for STAT (short turnaround time) samples. A predefined movement profile may also be utilized to build queues sorted by priority not necessarily by time of arrival as many other first in first out (FIFO) queues do.

In some cases, a predefined movement profile may be utilized to allow a laboratory product transport element to pass by a broken laboratory product transport element or overtake a slower moving laboratory product transport element. FIGS. 2A-2G provide such an example. In FIG. 2A, a first laboratory product transport element 730 may be following line 1310 and utilizing collision sensor(s) 737. A second laboratory product transport element 1330 may be in front of the first laboratory product transport element 730. In FIG. 2B, the first laboratory product transport element 730 detects second laboratory product transport element 1330 with collision sensor(s) 737. It may also determine that second laboratory product transport element 1330 is not moving, and may be broken, or may be going at a slower speed than the first laboratory product transport element 730. Using a predefined movement profile, the first laboratory product transport element 730 may leave line 1310 and follow instructions provided by the predefined movement profile. The predefined movement profiles may include semi-circles, arcs, and other shapes.

FIGS. 2C-2F show first laboratory product transport element 730 as it moves around the second laboratory product transport element 1330 using a predefined movement profile in the form of an arc. Once the first laboratory product transport element 730 returns to line 1310, as shown in FIG. 2G, it may continue to follow line 1310 utilizing its line following sensor(s) along with its collision sensor(s) 737. Predefined movement profiles can be performed without a lane or line, but it might be a beneficial to use the lane or line as a fine adjustment (combining predefined movement control with line following) for smooth movements.

In some embodiments, a predefined movement profile may be utilized when a laboratory product transport element determines that there is a bend, such as 90° degree bend, on its path. Near-field communication technology and/or RFID tags may be utilized to let the laboratory product transport element know that a bend exists on its path. FIG. 3 shows an example of utilizing a predefined movement profile for navigating a bend. Typically, if a laboratory product transport element 730 is not aware of moving through a bend 1440, it may try to move along straight segments. The line following sensors 742 can detect a different reflection and the laboratory product transport element 730 performs a corrective rotation movement. This is shown with path 1430. This sequence is reiterated until the next straight segment is arrived. With a higher polling rate, the more corrective actions can occur and the smoother the movement.

In some embodiments, a predefined movement profile can instead be utilized to create a smooth turning action for the laboratory product transport element 730. One example of a path that may result is shown for path 1435. A predefined movement profile may direct this movement for the laboratory product transport element 730 through providing instructions to accelerate an outer wheel to a certain velocity while decelerating an inner wheel. Knowing the bend radius and the wheel diameter, the laboratory product transport element 730 can perform a bend without line following using the motor encoder signals. In some cases, to compensate for slip effects or small wheel diameter differences, the line following sensors 742 can be used to adjust the predefined movements. In cases where the laboratory product transport element 730 follows a predefined (stored) trajectory, the line following sensors 742 can be used for fine adjustment of the movement with the same polling frequency as on straight tracks. When leaving or merging a straight lane, an increase of the moving speed may help to minimize the impact on throughput.

Predefined movement profiles may be utilized for other reasons. A predefined movement profile may be utilized for a laboratory product transport element to perform a U-turn. This may involve switching between lanes or lines with opposite moving directions. Sophisticated trajectories, such as spline-shaped trajectories, may be defined by predefined movement profiles. For example, a predefined movement profile may be utilized for high-speed ramp to and/or from high velocity lanes or sections. Predefined movement profiles may also be utilized to provide movement directions for a laboratory product transport element to enter or exit a specific portion of a transportation system, such as enter and leave a parking lot, a small one-position dead-end-streets that may require the laboratory product transport element to perform a 180° degree movement before leaving.

Predefined movement profiles may also be utilized along with collision sensors. For example, collision sensors can stay active during a movement of a laboratory product transport element based on a predefined movement profile in order to react to unexpected obstacles. A predefined movement profile can also direct a laboratory product transport element back on to a line to compensate for impreciseness that may come from controlling the movement with only the motor encoders.

Self-Diagnosis

Some embodiments may include methods, devices, and/or system configured for self-diagnosis. For example, a laboratory product transport element, such as laboratory product transport elements 30 and/or 730, may utilize one or more of its sensors or other components to perform a self-diagnosis of different aspects of the laboratory product transport element itself. In some cases, the laboratory product transport element may also be utilized to determine problems with a system, such as a transfer path arrangement, in which the laboratory product transport element may be operated, or a laboratory product such as a sample tube.

A system such as a transfer path arrangement or a sample transport system may need to have maximum reliability and uptime. Since failures are not completely avoidable, some embodiments that provide self-diagnosis can help to inform a user or the system or elements of the system about likely problems or give advice regarding how to eliminate a potential source of a problem. Different embodiments provide methods, devices, and/or systems to detect errors before they may result in a problem or process interruption. Embodiments may overcome problems with some solutions that may be either too expensive, require additional sensors, or may provide no diagnosis functions at all. Missing diagnosis functions can often lead to a system interruption as the inspection might be neglected especially in areas which are not easy to access.

Some embodiments may provide methods, devices, and/or systems that may only utilize sensors and/or other elements of a laboratory product transport element or a system which may already be provided for the movement and the line following of the laboratory product transport elements. For example, a laboratory product transport element can perform a self-diagnosis by performing an initialization routine to check the function of the line following and/or the collision sensors in a defined area. In some cases, the laboratory may perform the self-diagnosis operation at one or more charging spots. A laboratory product transport element may perform a 360° rotation where all of the line following sensors pass over white and black areas. In case one or more of the sensors is defective or possibly heavily dirty sensor may show no signal change at all when moving from a black to white area or vice versa. This information may be sent to a user through different communication devices of the system. In cases where one or more sensors may be partly dirty, a signal from a sensor may be reduced and/or provide an unclear signal change. In some embodiments, if enough signal change is left, a calibration of the sensors may be performed to compensate for the contamination or other problem with the sensor. In some cases, it may be possible to move the laboratory product transport element to a user interface location where the user can access the laboratory product transport element and clean and/or otherwise repair the laboratory product transport element. In some cases, the laboratory product transport element or the system may send a signal informing the user about the position of the dirty or defective laboratory product transport element. The signal may include information regarding the need for one or more sensors to be cleaned or repaired.

Some embodiments may utilize sensors of the laboratory product transport element to recognize unexpected gaps, stains, or other problems on the lane, surface, or other locations in the system such as a transfer path arrangement. Information may be reported, providing the location back to a central controller or user. In case multiple laboratory product transport elements detect the same failure, a user may get informed to control the announced section of the track. In case only one laboratory product transport element can see the failure, a user can be informed to control the specific laboratory product transport element.

Figure 4A:
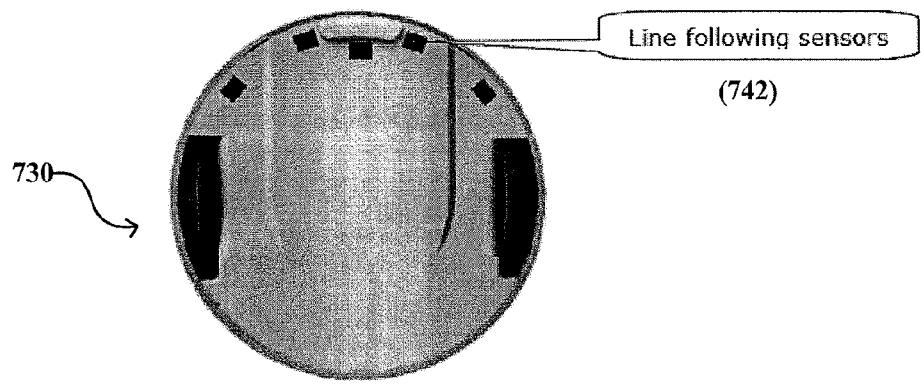
FIGS. 4A, 4B, and 4C show an example of self-diagnosis of laboratory transport system in accordance with various embodiments.
Figure 4B:
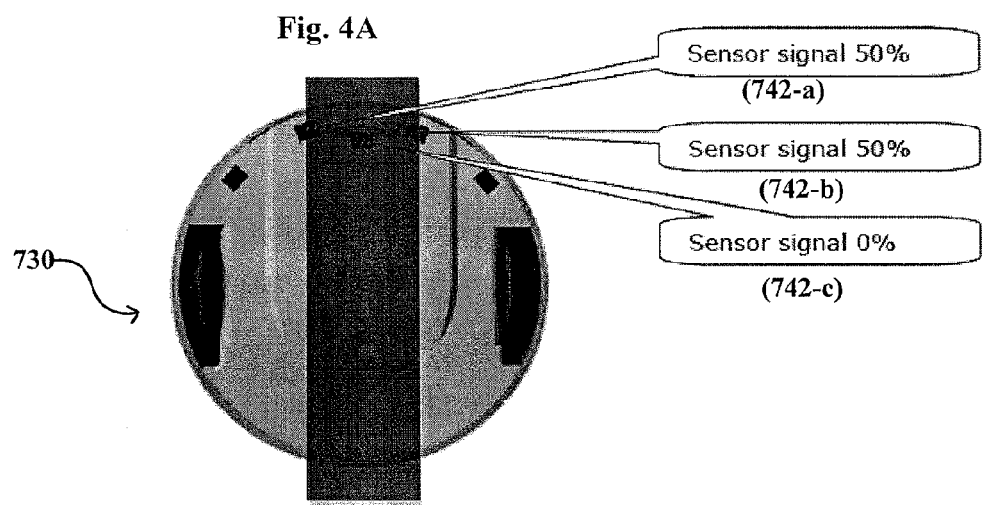
Figure 4C:
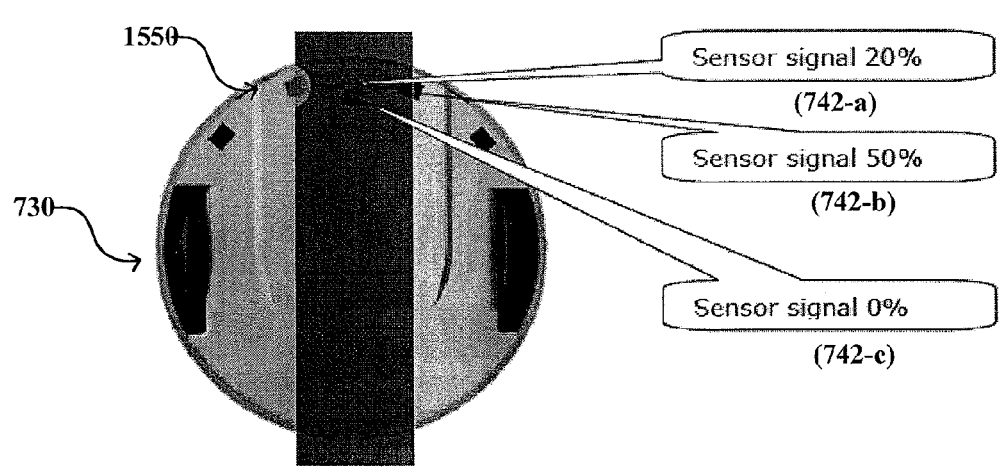

FIGS. 4A-C provide an example of how line following sensors 742 of laboratory product transport element 730 may be utilized to recognize problems with either the laboratory product transport element itself or a surface on which the laboratory product transport element may be traveling. FIG. 4A shows a bottom surface of a laboratory product transport element 730 with multiple line following sensors 742. Laboratory product transport element 730 may recognize abnormal sensor signals in different ways including the following. In FIG. 4B, line following sensors 742-a, 742-b, and 742-c detect a normal signal state from left to right, reflected as 50%-0%-50% (in this example, the two outer sensors 742-a and 742-b can have a 100% signal when added). FIG. 4C shows an example where a temporary 20%-0%-50% ratio could be an indication for a stain 1550 on the left edge of the lane. Other ratios may reflect other problems with the surface of the laboratory product transport elements. For example, if the ratio are different between the outer sensors 742-a and 742-c for a period of time, this may reflect a problem with one of the line following sensors themselves.

Self-diagnosis of a laboratory product transport element may utilize other aspects of the device, such as the drive devices and/or movement devices of the laboratory product transport element. For example, a comparison of one or more drive device encoder signals and line following sensor signals may discover wear on a movement device. A different diameter of a movement device, such as a wheel, may use different drive device speeds on known straight track segments. In case the difference reaches a definable threshold, a user may be informed to change the movement device. In some cases, the drive device may alter its speed to accommodate for the wear discovered on the movement device.

Similarly, a laboratory product transport element may travel along a well-known distance and count the drive device encoder steps. A worn movement device may lead to a smaller outer diameter and therefore more encoder steps per distance. In case the number of encoder steps exceeds a definable threshold, the user may again be informed of the wear and the possible need to replace the movement device. In some cases, the drive device may compensate for the wear of the movement device.

Some embodiments may measure or otherwise determine drive device current or power usage to provide a stickiness measurement or other measures of the functionality of the laboratory product transport element or a surface of a transfer path arrangement. For example, spilled serum and/or blood can generate a kind of "sticky" surface increasing the necessary drive device force to move the laboratory product transport element. A measured change in the current or power consumption used to power the drive device may be utilized to determine such potential problems with one or more surfaces of a transfer path arrangement.

The self-diagnosis embodiments may provide real-time feedback of transfer path or laboratory product transport element problems. As a result, contamination or other problems may be reduced to a minimum.

Kidnapping Detection

Some embodiments may include methods, systems, and/or devices for kidnapping or unexpected removal detection of a laboratory product, such as a sample container 50, and/or laboratory product transport element, such as laboratory product transport elements 30 and/or 730. Additionally, the unexpected removal or shaking of a centrifuged tube can cause malfunction in later processing steps, thus kidnapping detection may be able to prevent such malfunction. Some embodiments of the invention may reduce concordance failures or process problems in an automated lab-environment caused by illegal user intervention and/or foreseeable misuse. Other embodiments of the invention may provide for constantly controlling the presence of a laboratory product in a laboratory product transport element as well as the presence of the laboratory product transport element on a transfer path arrangement.

Some embodiments that include kidnapping detection may provide advantages over other laboratory transport systems that may merely check the presence of a laboratory product and/or read laboratory product barcode at functional spots in the system, such as diversion, point in space, load and unload positions. For example, when a laboratory product's presence is checked by the system at certain places, a temporary removal of the laboratory product may not be detectable. Reading the barcode on every diversion and functional spot may solve the problem, but can be expensive. In addition, some embodiments may provide advantages over systems that may merely rely on the user not having access to in-flow laboratory products.

Embodiments may include sensor systems and/or devices to control the laboratory product presence in the laboratory product transport element and/or the uninterrupted contact between the laboratory product transport element and a transfer path arrangement. Since laboratory product transport elements can have their own processors, each may be capable of detecting and/or storing information regarding different situations in its memory and communicate one or more error signals or messages. These error signals may be transmitted using a variety of different channels including, but not limited to, wireless connections such as near-field communication spots.

For cases where a laboratory product may be removed from a laboratory product transport element, different methods, systems, and devices may be utilized to detect such removal. In one embodiment, an optical sensor may be utilized. An optical sensor may be coupled with a laboratory product holder for example, of laboratory product transport element. Such an optical sensor may include a light barrier in the laboratory product holder in some cases. In another embodiment, a mechanical sensor may be utilized. For example, a mechanical sensor may become active when there is a laboratory product in the holder. When a laboratory product is removed, the mechanical sensor may deactivate, thereby sending a signal indicating that the laboratory product has been removed from the holder. In some cases, an RFID-tag or other indicator may be coupled to the laboratory product. The laboratory product transport element may be configured to read the tag or indicator to determine its presence in the holder and can provide an error signal when it no longer identifies that the tag or indicator in the holder.

Some embodiments may be configured to determine laboratory product transport element removal from a laboratory transport system, such as from a surface of a transfer path arrangement. In one example, line following sensors, such as line following sensors 737, of the laboratory product transport element may be utilized to detect the removal of the laboratory product transport element. For example, if there is no detected reflection on the sensors and/or the reflection pattern does not make sense for a pre-determined time (e.g., one second), then this may indicate that the laboratory product transport element has been removed. In another example, a drive device measurement (e.g., a current measurement) may be utilized. For example, if the actual drive device current is much lower than usually necessary to move the laboratory product transport element, this may indicate that the laboratory product transport element has been lifted up in that moment. In some cases, a central controller may be utilized to detect removal of the laboratory product transport element. For example, a central controller may verify expected laboratory product transport element sequence at nodes in the system. In case a laboratory product transport element does not appear within a certain (configurable) time, the system can recognize the laboratory product transport element as removed. In some cases, a status of a laboratory product transport element may be unclear even when it appears later in the laboratory product transport system. This can occur if a user puts a laboratory product transport element back on the transfer path arrangement.

When a system indicates that laboratory product and/or laboratory product transport element is removed, a status of the laboratory product or laboratory product transport element may be referred to as unclear. Planned processes for the laboratory product may be interrupted as a result. In some cases, the laboratory product transport element and/or laboratory product may be routed to an error workplace, a special inspection spot, or other locations where the user may need to decide how to continue with the laboratory product. In one example, where there are no double barcodes, the laboratory product transport element may also move to a place where the laboratory barcode can be verified, and as such, a temporarily removed laboratory product can be processed further immediately.

In some embodiments, a laboratory product transport element may remember the location of the occurrence of its removal or the removal of its laboratory product. The laboratory product transport element may transfer that information to a central controller, which in some cases may occur at near-field communication spot. This may allow for a laboratory product loss without user interaction (e.g., laboratory product collapse) that can lead to a user notification after a view seconds and prevent a wide distribution of possibly contaminated material.

Embodiments that may allow for the detection of a removed laboratory product and/or laboratory product transport element may also be utilized to verify successful processes. For example, the methods and devices for detection of laboratory product removal may also be utilized in some cases to verify a successful laboratory product load, through a change from an empty state to a loaded state. Similarly, the successful removal of a laboratory product may be indicated with a change from loaded to empty. In some cases, embodiments may also be able to determine if a laboratory product has been successfully decapped. This may help avoid the loss of a sample in case the complete laboratory product is removed instead of the cap only. Some embodiments may be able to determine information regarding where a laboratory product transport element may be reinserted into a system. In some cases when a laboratory product transport element is removed from the system, it may be returned in a random place in the system. Since the laboratory product transport element may know its "unclear" status, the laboratory product transport element can be routed to the appropriate place in the system. In some cases, this routing may be initiated when the laboratory product transport element makes contact with a communication device in the system, such as a near-field communication spot.

Embodiments for the detection of the removal and/or replacement of laboratory products and/or laboratory product transport elements can also be used in a conventional laboratory transport system along with a system such as the transfer path arrangement. In some cases, a laboratory product and/or laboratory product transport element may have some identifier, such as an RFID tag, on which a controller within the laboratory product transport element can write a status change. Information about a temporary removal of a laboratory product may be detected at a next RFID spot. In some embodiments, power for the writing can either be supplied by energy accumulator, such as a battery, in the laboratory product transport element or by a piezo element, which can use the movement of the elements of the laboratory product holder to produce enough power for the controller to write the status change to the RFID. Some embodiments may combine the one or more of the sensors of the laboratory product transport element with a power supply to store the information independent from an external or battery created power supply.

Fine Positioning and Lift-Off Prevention

Some embodiments provide methods, systems, and/or devices for fine positioning and/or lift-off prevention of a laboratory product transport element, such as laboratory product transport elements 30 and/or 730. In some situations, laboratory product transport elements within a laboratory transport system, such as a transfer path arrangement, may need to be positioned very precisely or at least with a highly repeatable accuracy at one or more positions within the system. Several embodiments provide for performing the positioning with the required accuracy to achieve fine positioning. In addition, there are situations or locations within a system that may require lift-off prevention for the laboratory product transport element. For example, a folded or damaged label on a laboratory product might stick so tightly within a sample holder of a laboratory product transport element that the weight of the laboratory product transport element may not be not sufficient to provide for the laboratory product transport element to stay on a surface of the system when the laboratory product is removed.

Fine positioning and lift-off prevention methods and techniques may be utilized separately or in combination. In some cases, a laboratory product transport element may include protrusions on one or more sides of the laboratory product transport element to facilitate fine positioning and/or lift-off prevention. Slots or other elements may be provided on different aspects of the laboratory transport system, such as a transfer path arrangement, that may couple with the protrusions. For example, a laboratory product transport element may be moving along a surface until it reaches a certain point and then performs a rotation. When the protrusions have made contact with the slots in the transfer path arrangement, the laboratory product transport element may force itself to a defined position. Assuming the protrusions are shaped in a suitable manner, both the X and Y position can be reached at once. On top of that, the upper part of the transfer path arrangement's slots can prevent the laboratory product transport element from lift off in case the laboratory product is removed at that spot.

In some cases, there may be a gap between side of laboratory product transport element and a portion of a transfer path arrangement in order to give the laboratory product transport element some space for corrective movements while following a line. It may not be necessary or desired to have physical contact there as it may produce unnecessary friction and abrasion. In some embodiments, in front of a functional spot, portions of the transfer path arrangement can narrow down so that a laboratory product transport element can still pass through. As long as the line following is precise enough, there may not be contact between the laboratory product transport and the side portions of the transfer path arrangement.

The actual positioning in the direction of transport can be realized by one or a combination of the following methods. In some embodiments, lift-off prevention may be performed in additional, but different locations, such as functional spots. However, fine positioning may be utilized for the laboratory product transport element may not require lift-off prevention.

Fine positioning may be achieved using the line following sensors of a laboratory product transport element in some embodiments. For example, a position indicator, such as window 1670, in a center line 1611 may be provided as shown in FIGS. 5A and 5B. Laboratory product transport element 730 may include multiple line following sensors 742, which may be in line such as sensors 742-*a* and 742-*b* that can detect the rims of the window 1670. The fine positioning can be reached when both sensors 742-*a* and 742-*b* deliver the same signal. This use of line followings sensors 742 and window 1670 may provide a system that is independent from the absolute reflectivity, which may decrease over the time. In some cases, it may be desirable to use two sensors, such as 742-*c* and 742-*d*, at the edges of the line for correct rotation alignment. In some embodiments, markers may be placed outside a line of the transfer path arrangement, providing markers for outer sensors, such as sensors 742-*e* and or 742-*f*. A laboratory product transport element may stop when one or more outer sensors detect the markers on the surface of the transfer path arrangement. In another case, a unique pattern of markers may be provided on a surface of the transfer path arrangement, such as 1-0-1-0-1, providing an indication of the functional spot for the line sensors to detect and determine the location for fine positioning.

Near-field communication devices may be utilized for fine positioning for some embodiments. A laboratory product transport element, such as laboratory product transport element 730, may measure a field signal strength or detect the start point of communication of a near-field communication device to determine the laboratory product transport element's position. In some cases, positioning information provided through communication with a near-field communication device may provide a rough positioning. This positioning may be coordinated in combination with the line following sensors, such as line following sensors 742, to provide fine positioning in some cases. For example, near-field communication may initiate processes like slowing down the laboratory product transport element and then starting to increase line following sensor polling frequency for the fine positioning to be achieved.

One or more collision sensors, such as collision sensors 737, of the laboratory product transport element may also be utilized for fine positioning in some cases. Collision sensors may be utilized to detect a defined obstacle to perform the fine positioning. For example, the laboratory product transport elements can move into a dead-end street slot and stop at a defined distance with respect to a wall or other barrier structure of the system. After the process, the laboratory product transport element can move backwards to make the position available for a next laboratory product transport element in some cases.

In some embodiments, an LED receiver in a laboratory product transport element may receive positioning from an LED in the transfer path arrangement. For example, a LED (visual light or infrared (IR), for example) may be placed at a functional spot in the bottom or in the borders of the transfer path arrangement. The laboratory product transport element may include a light sensitive array that can measure the light intensity on the array. When the maximum signal appears at the center field(s) of the array, the laboratory product transport element may be on the correct position. In some cases, the laboratory product transport element can have the ability to move forth and back to find the maximum. In a preferred embodiment, a laboratory product transport element may be configured to reduce corrective movements to a minimum to reduce the amount of time required to achieve a fine position.

Figure 6A:
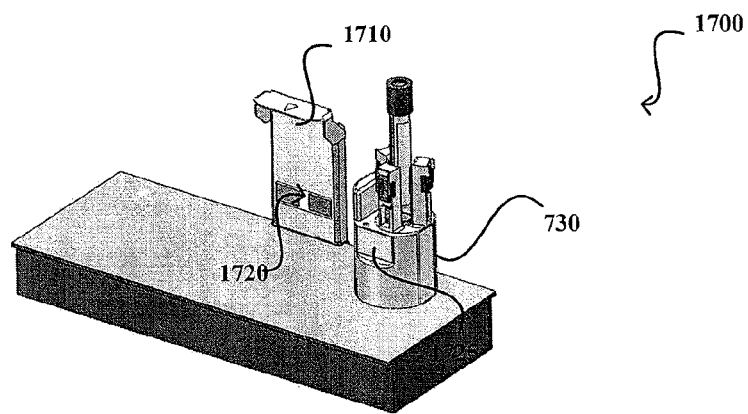
FIGS. 6A, 6B, 6C, and 6D show another example of fine positioning of a laboratory product transport element in accordance with various embodiments.
Figure 6B:
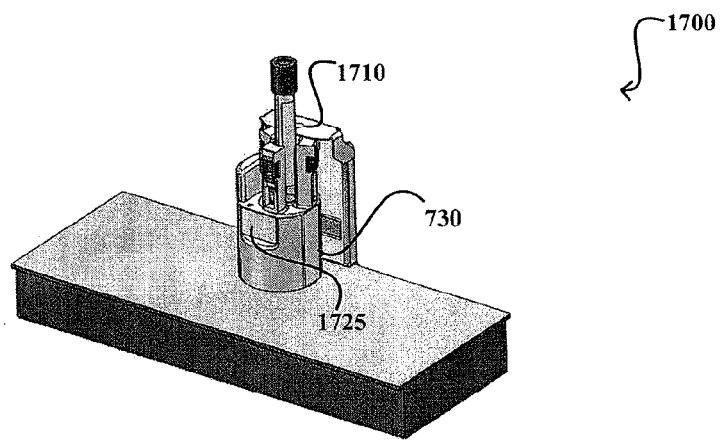
Figure 6C:
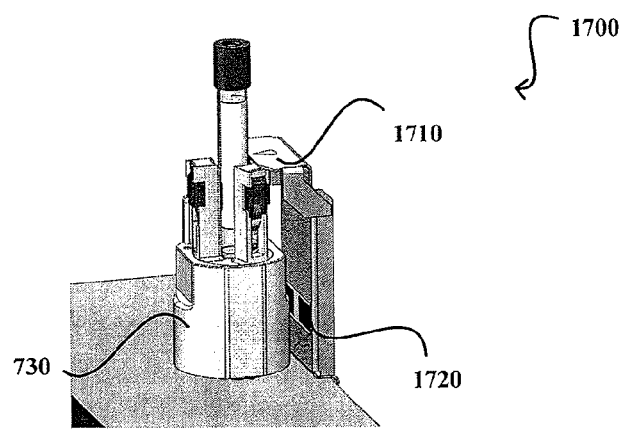
Figure 6D:
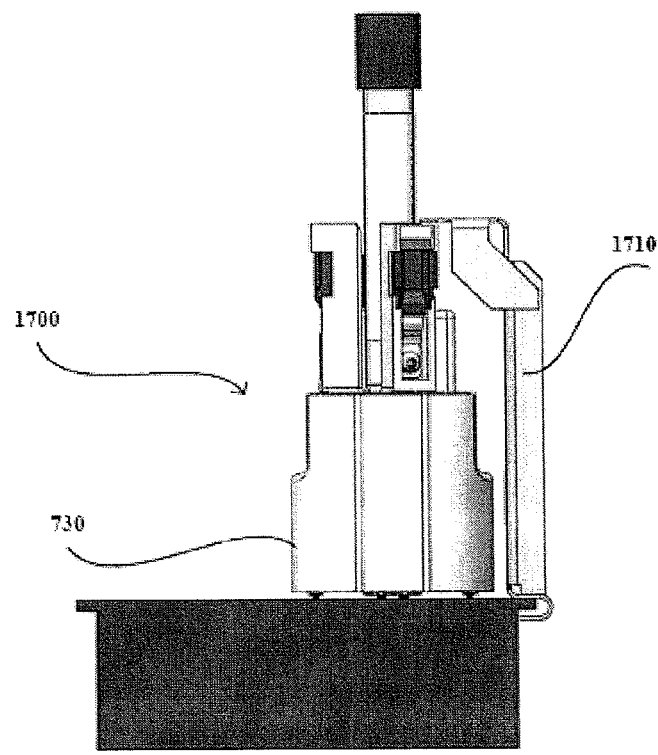

Fine positioning may also be achieved using one or more optical sensors on one or more sides of a laboratory product transport element in some embodiments. Optical sensors positioned on the side of a laboratory product transport element may provide some advantages because of the easy adjustment of a position marker since it can be independent from a surface of the laboratory transport system. In one embodiment, sensors can include two or more reflective sensors configured to detect a gap at a marker at the side of the track. FIGS. 6A-6C show one such an example. FIG. 6A shows a transfer path arrangement 1700 that includes a fine positioning structure 1710 that includes one or more fine positioning markers 1720. In this example, fine positioning marker 1720 utilizes a pattern that includes a gap that may be detected by reflective sensors 1725 of laboratory product transport element 730. FIGS. 6B and 6C show laboratory product transport element 730 in position when it has detected the positioning marker 1720. In some cases, the gap may be a highly reflective surface separated by absorbing surfaces. Fine positioning structure 1710 may be moveable in some cases. In another embodiment, a fork light barrier may be provided that is interrupted by a cantilever piece from the side of the track. In another embodiment, a Hall effect sensor in the laboratory product transport element and magnets at the side bracket of a transfer path arrangement may provide for fine positioning. Also, active LEDs in the side bracket of a transfer path arrangement and IR detectors in the laboratory product transport element may be utilized for fine positioning in some embodiments. FIG. 6D shows a side view of the transfer path arrangement 1700 with fine positioning structure 1710 and laboratory product transfer element 730. The top of positioning structure acts as lift-off prevention.

Some embodiments may include laboratory product transport elements that are also configured for lift-off prevention. FIGS. 7A-7D, for example, provide an embodiment that can provide both fine position and lift-off prevention. FIG. 7A shows a laboratory product transport element 730 that includes multiple lateral protrusions 1810. For this embodiment, lateral protrusions 1810 may be lateral rails. Other embodiments may include lateral protrusions 1810 with other configurations, such as lateral posts. Lateral protrusions 1810 may be coupled with housing 1805 of laboratory product transport element 730. In some cases, lateral protrusions 1810 may be fixed or made part of the housing 1805. In some embodiments, lateral protrusions 1810 may be adapted to be connected and disconnected from housing 1805.

FIG. 7B shows an example of a laboratory product transport element 730 following a line 1811 on a transfer path arrangement. FIG. 7B shows a rail element 1820 that is part of the transfer path arrangement. In some embodiments, rail element 1820 may be mountable on the transfer path arrangement such that it may be attachable and/or removable from the transfer path arrangement. Rail element 1820 includes one or more slots 1830 that may be configured to cooperatively work with lateral protrusions 1810 by receiving the lateral protrusions 1810. Some embodiments may include other elements coupled with rail element 1820 that may be configured to couple with the lateral protrusions 1810. FIG. 7C shows the location where laboratory product transport element 730 may determine that it is at a fine positioning location. At this point, laboratory product transport element 730 may begin rotating 1840 such that lateral protrusion 1810 may couple with slots 1830 of rail element 1820. FIG. 18D shows the position where the lateral protrusion 1810 meets portion 1850 of the rail element 1820 that defines a portion of the slot 1830, effectively stopping the laboratory product transport element 730 from rotating further. This position may be a predefined position for the laboratory product transport element 730. Furthermore, the lateral protrusion 1810 coupled with slot 1830 may now provide for lift-off protection for the laboratory product transport element 730.

FIGS. 8A-8D provide another embodiment that can provide both fine position and lift-off prevention. FIG. 8A shows a laboratory product transport element 730 that includes multiple groove structures 1912. For some embodiments, groove structure 1912 may be a hook structure. Other embodiments may include groove or hook structures 1912 with other configurations. Groove structure 1912 may be part of the housing 1905 of the laboratory product transport element 730.

FIG. 8B shows an example of a laboratory product transport element 730 following a line 1911 on a transfer path arrangement. FIG. 8B shows a rail element 1920 that is part of the transfer path arrangement. In some embodiments, rail element 1920 may be mountable on the transfer path arrangement such that it may be attachable and/or removable from the transfer path arrangement. Rail element 1920 includes protrusion elements 1921 that may couple with groove structure 1912 of the laboratory product transport element 730. Protrusion element 1921 may also be configured in some embodiments to be attachable and/or removable from rail element 1920.

FIG. 8C shows the location where laboratory product transport element 730 may determine that it is at a fine positioning location. At this point, laboratory product transport element 730 may begin rotating such that groove structure 1912 may couple with a protrusion element 1921.

FIG. 8D shows the position where the groove structure 1912 meets protrusion element 1921 of rail element 1920, effectively stopping the laboratory product transport element 730 from rotating further. This position may be a predefined position for the laboratory product transport element 730. Furthermore, the groove structure 1912 coupled with protrusion element 1921 may provide for lift-off prevention for the laboratory product transport element 730.

In some embodiments, a signal of line-following sensor can also be used to determine the actual position of the laboratory product transport element and transfer this information to a central controller. The control unit then can use this value and reposition a robot or other accessing device to the new position. In that case, performing a positioning movement is not necessary for the laboratory product transport element at all. Some embodiments may use active track components like active driven clamps forcing the laboratory product transport element to the exact position and hold it firmly during the process.

Throughput Control at Intersections

Some embodiments provide methods, systems, and/or devices for managing throughput control at intersections. Embodiments may provide for a laboratory transport system to reach a maximum throughput control with a minimum stress for different laboratory products. Embodiments of the invention can provide for handling traffic at intersections where there may be a potential collision between laboratory product transport elements. Embodiments of the invention may provide techniques to gain maximum throughput using a combination of near-field communication devices and collision sensors.

Intersections are often the bottleneck for throughput in laboratory transport systems. For example, laboratory product transport elements can get either stopped unnecessarily or at least longer than necessary at intersections, which can lead to queues and undesirable motion for a laboratory product when a laboratory product transport element meets another transport element at the end of a queue. Embodiments can allow for multiple laboratory product transport elements at intersections.

Embodiments provide methods, systems, and device that can utilize a combination of near field communication and collision control sensors. In some cases, the collision sensors may be analogue sensors. At certain points in time and/or location, a laboratory product transport element may be switched from near-field communication controlled to collision sensor controlled and vice-versa. Embodiments can be controlled in a way that two collision sensors can avoid a deadlock situation where rivo laboratory product transport elements each wait for the other one to disappear. Moreover, in cases where leaving or merging laboratory product transport elements use higher speeds in turns, the impact to the throughput can be further minimized.

Embodiments may allow more than one laboratory product transport element in an intersection area when the collision control works properly. In some cases, the travel time for taking an exit at an intersection from a decision point to a safe position may take a certain amount of time (e.g., greater than 1 second) without any communication latency. Repeatability of the actual position of different laboratory product transport elements at the moment of the first near-field communication device contact may be important in different situations. For example, a near-field communication device may need to mark the "stop" or "wait"

position. A laboratory product transport element may need to communicate via a near-field communication device in the stop position. The positions of the near-field communication device (which may be referred to as near-field communication coils in some cases) in the track of a laboratory transport system may have a big influence to the throughput. A diversion can be controlled without mandatory stops. The collision sensors can control the flow.

Near-field communication devices can have different functions. For example, a near-field communication device may include a landmark function, where in front of a diversion, the laboratory product transport element may need to decide whether it stays on the track or takes the exit. Other function may be a stop-only-on-demand function, which may be utilized in front of a merge to avoid deadlock and to control priority. Another function may be an exit confirmation, which may provide for information for the traffic control after a junction (e.g. to calculate a queue size, etc.). Another function may be an exit confirmation after merge function to allow the a next laboratory product transport element to enter the merge-area. Some functions may refer to specific functional spots (put tube, de-cap, re-cap, etc.) which may also act as a stop function.

A laboratory product transport element may utilize its line-following and collision sensors. When a laboratory product transport element moves close enough to a near-field communication device of the laboratory transport system, it may receive a variety of signals that may help direct the laboratory product transport element through an intersection. These signals may include stop signals. The signals from the near-field communication device may rule the collision control detection results from a collision sensor of the laboratory product transport element, which may indicate an open passage without recognizing that another laboratory product transport element may be in the process of entering the intersection, but is outside the range of the collision sensor. Note that for energy savings reasons, the collision sensors may be switched off during times when the laboratory product transport element may be stopped by a signal from a near-field communication device. Similar techniques may be utilized for the line-following sensors of a laboratory product transport element.

Near-field communication devices located at different positions within a laboratory transport system and laboratory product transport elements allow for two-way communication between these devices. In some embodiments, near-field communication devices of the laboratory transport system may be in communication with each other and/or a central controller. While the following embodiments provide examples with near-field communication devices, some embodiments may utilize RFID tags, barcodes, alternating line patterns, etc., although these embodiments may or may not provide for two-way communication.

FIGS. 9A-9H show one example of utilizing throughput control methods in accordance with various embodiments. FIGS. 9A-9H provide an example where one or more laboratory product transport elements 730 can communicate with near field communication devices associated with one or more intersections of a laboratory transport system.

Figure 9A:
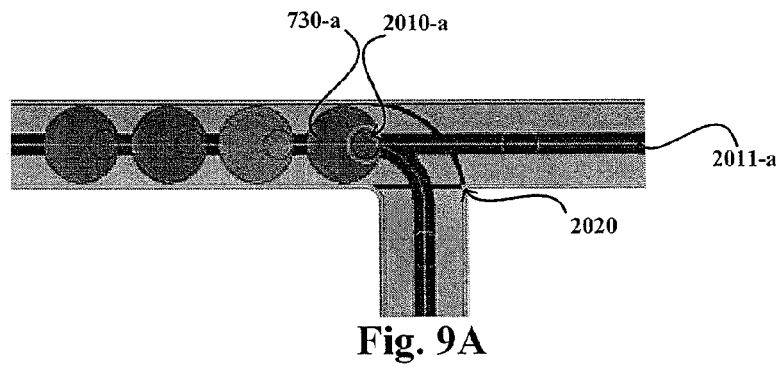
FIGS. 9A-9J show an example of throughput control at an intersection, a diversion example in this case, in accordance with various embodiments.

FIGS. 9A-9H show an example of throughput control at an intersection in accordance with various embodiments of the invention. This example may be referred to as a diversion embodiment. In FIG. 9A, multiple laboratory product transport elements 730 are shown traveling along a transfer path, following line 2011-*a*. Several near field communication devices 2010 are located before and after an intersection 2020.

FIG. 9A shows laboratory product transport element 730-*a* in communication with near field communication device 2010-*a* located along line 2011-*a*, where it may receive information. Laboratory product transport elements 730 may include a near-field communication device or component to receive from or to transmit to near-field communication devices such as 2010. In this case, laboratory product transport element 730-*a* may receive instructions to proceed through the intersection 2020.

Figure 9B:
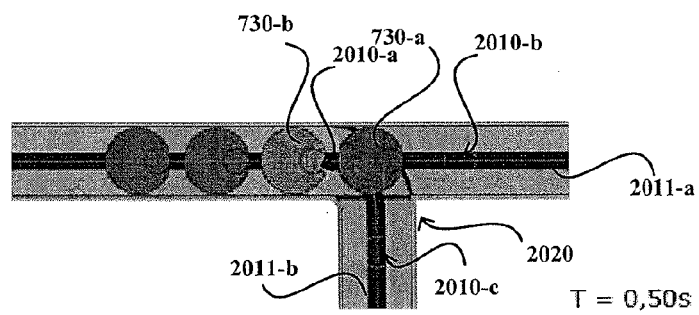

FIG. 9B shows laboratory product transport element 730-*a* proceeding through the intersection 2020 while maintaining itself on direction line 2011-*a*. In addition, laboratory product transport element 730-*b* begins communication with near field communication device 2010-*a*. Laboratory product transport element 730-*b* can begin receiving information about the location. In this example, laboratory product transport element 730-*b* may have information to turn right at the next exit or intersection 2020.

Figure 9C:
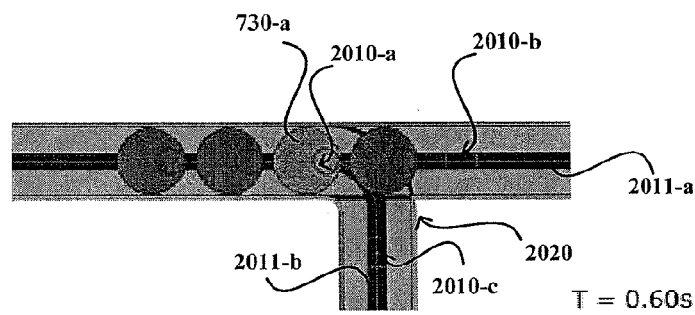

FIG. 9C shows laboratory product transport element 730-*b* having proceeded further over the near field communication device 2010-*a* where it has received information from the near field communication device 2010-*a*.

Figure 9D:
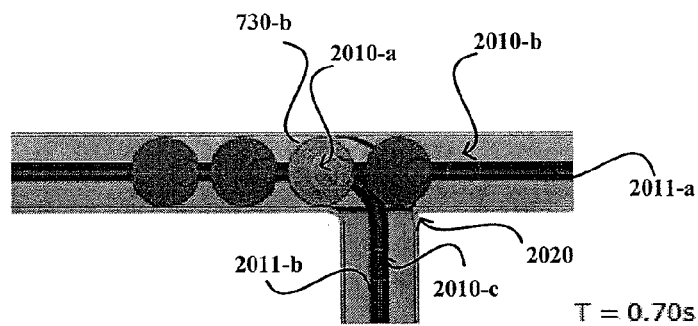

FIG. 9D shows the point where laboratory product transport element 730-*b* is at the point where it may be able to communicate with the near field communication device 2010-*a* before it proceeds too far to communicate with near field communication device 2010-*a*. This may be a last point to update the laboratory product transport element's 730-*b* route plan through the intersection 2020.

Figure 9E:
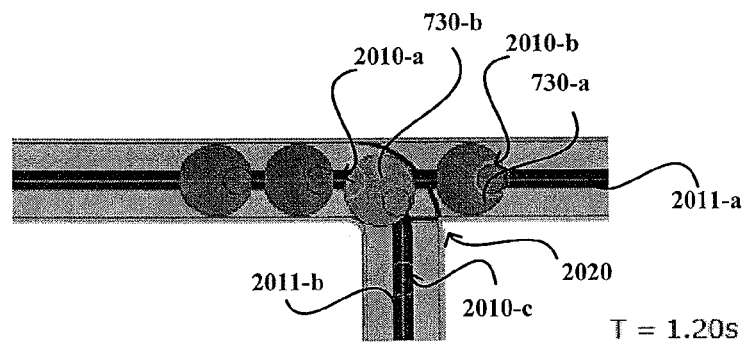

In FIG. 9E, laboratory product transport element 730-*a* may communicate with near-field communication device 2010-*b*, where it may confirm that it is exiting from the intersection 2020 region. This may help inform the traffic control.

Figure 9F:
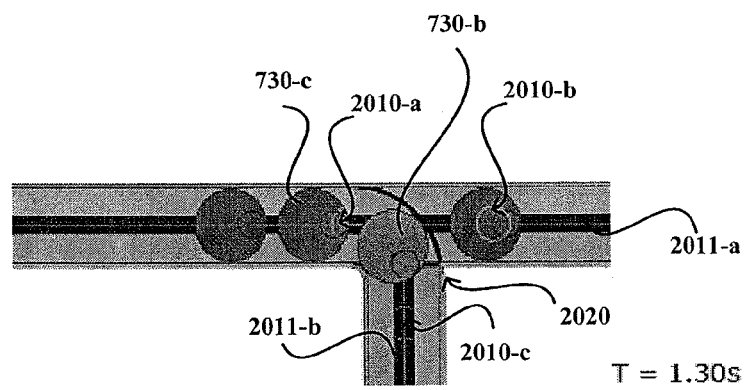

In FIG. 9F, laboratory product transport element 730-*c* may start communicating with near-field communication device 2010-*a*, while laboratory product transport element 730-*b* continues to turn at intersection 2020 onto line 2011-*b*.

Figure 9G:
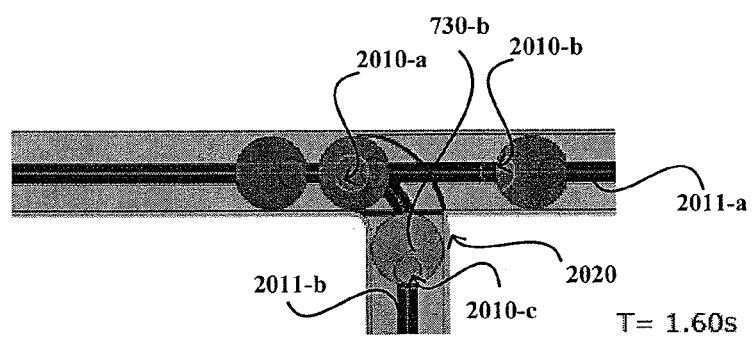

FIG. 9G shows the point where laboratory product transport element 730-*b* can communicate with near-field communication device 2010-*c* along line 2011-*b*, confirming its exit from intersection 2020.

Figure 9H:
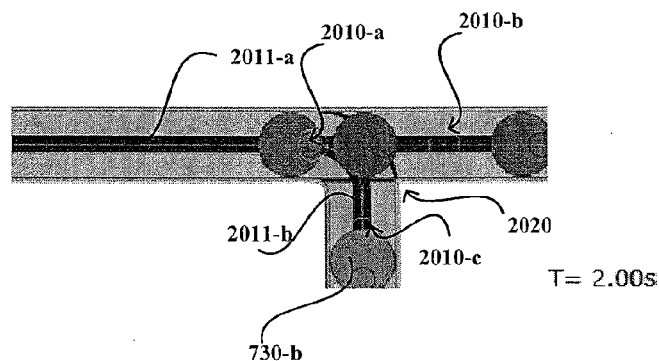

FIG. 9H shows an example further in time after laboratory product transport element 730-*b* has finished exiting intersection 2020 and continues to proceed along line 2011-*b*.

Figure 9I:
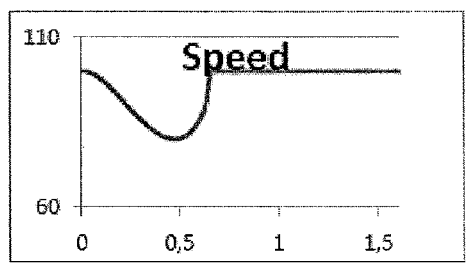
Figure 9J:
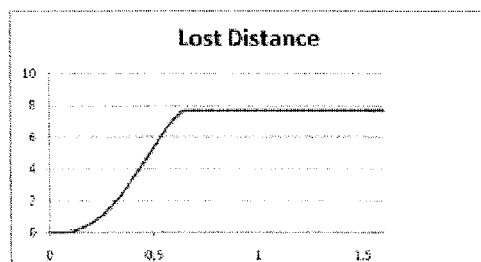

FIGS. 9I and J show graphs reflecting the speed and lost distance for a laboratory product transport element 730-*c* that may be following laboratory product transport element 730-*b*.

FIGS. 10A-10F show another example of throughput control at intersections in accordance with various embodiments. This example may be referred to as a merge example. A merge may require multiple stop positions for the laboratory product transport elements 730. They may be one of a main lane, such as along line 2111-*a*, to avoid deadlocks. A common exit near-field communication device, such as 2110-*b*, may also be used. In the case where there are no laboratory product transport elements 730 on the other lane or line, a laboratory product transport element 730 can pass without temporary stopping.

Figure 10A:
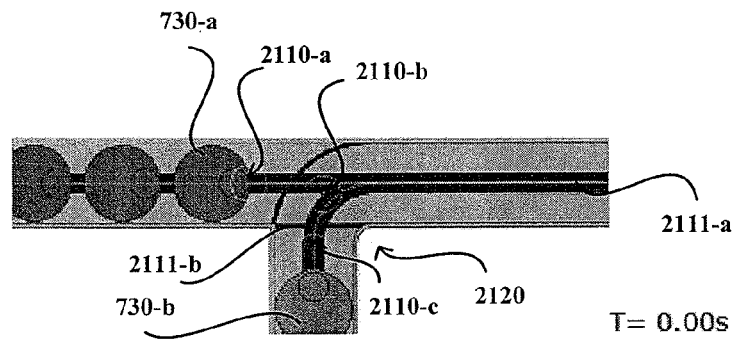
FIGS. 10A-10F show another example of throughput control at an intersection, a merge example in this case, in accordance with various embodiments.
Figure 10B:
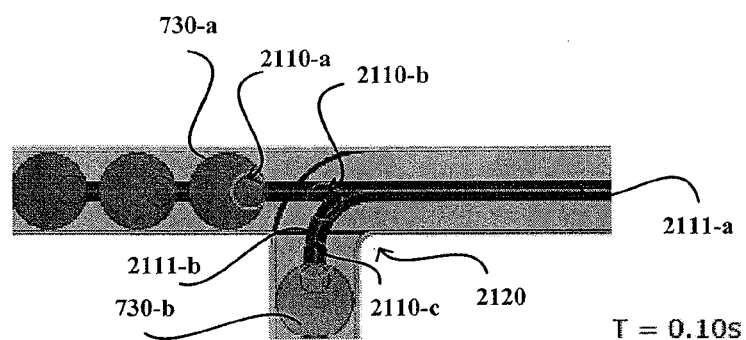
Figure 10C:
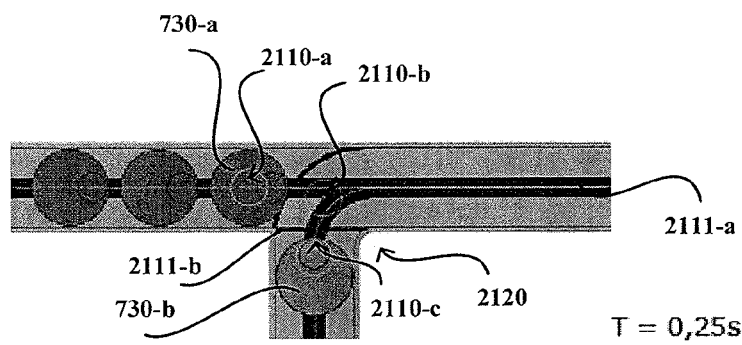

In this merge example, two laboratory product transport elements 730-*a*, 730-*b* may be stopped, one on line 2111-*a* and one 2111-*b*. In FIG. 10A, laboratory product transport element 730-*a* may start communication with near-field communication device 2110-*a*. In FIG. 10B, laboratory product transport element 730-*a* may get clearance from near-field communication device 2110-*a* to enter the merge area 2120. In addition, laboratory product transport element 730-*b* may start communicating with near-field communication device 2110-*c*. In FIG. 10C, laboratory product transport element 730-*b* receives information from near-field communication device 2110-*c* to stop, and thus it stops.

Figure 10D:
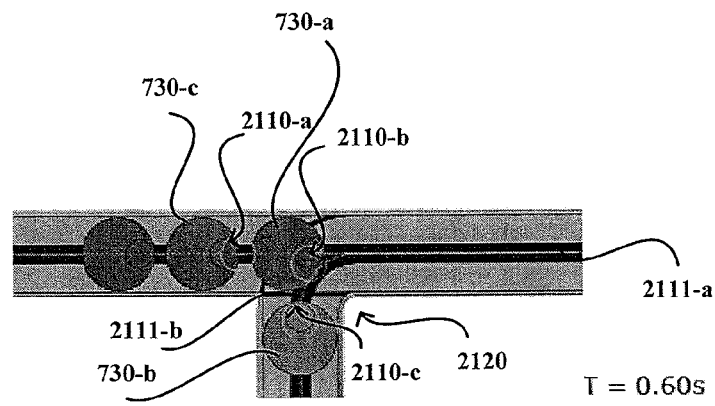

FIG. 10D shows the point where laboratory product transport element 730-*a* may start communicating with near-field communication point 2110-*b* at the merge area 2120. Laboratory product transport element 730-*a* can confirm that it is exiting the merge area 2120. At this point, laboratory product transport element 730-*a* is now in the collision control area of laboratory product transport element 730-*b*. As result, laboratory product transport element 730-*b* can get the clearance to go from near-field communication point 2110-*c*. Note that if the near-field communication point 2110-*a* were positioned further to the left along line 2111-*a* and therefore already communicating with laboratory product transport element 730-*c*, the traffic control could give priority to the laboratory product transport element 730-*c*. In this example, laboratory product transport element 730-*c* is just beginning communication with near-field communication device 2110-*a*, where it receives a stop signal as laboratory product transport element 730-*b* is entering the merge area 2120.

Figure 10E:
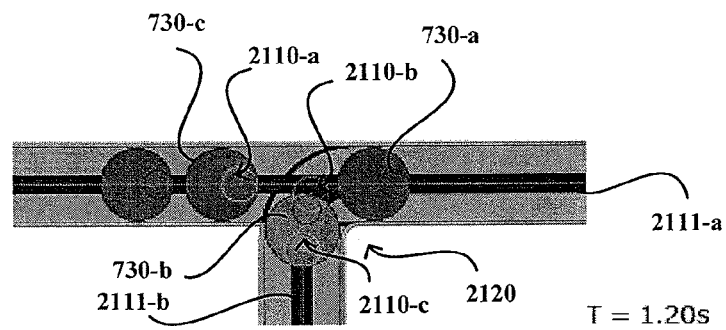

FIG. 10E shows laboratory product transport element 730-*b* entering merge area 2120 where it may begin following line 2111-*a*. It may begin communicating with near-field communication device 2110-*b*. As soon as laboratory product transport element 730-*b* can give an exit confirmation to near-field communication point 2110-*b*, laboratory product transport element 730-*c* may receive a clearance signal from near-field communication device 2110-*a*. Laboratory product transport element 730-*c* may proceed, but may go at a slow speed as its collision sensors may keep it a certain distance from laboratory product transport element 730-*b*.

Figure 10F:
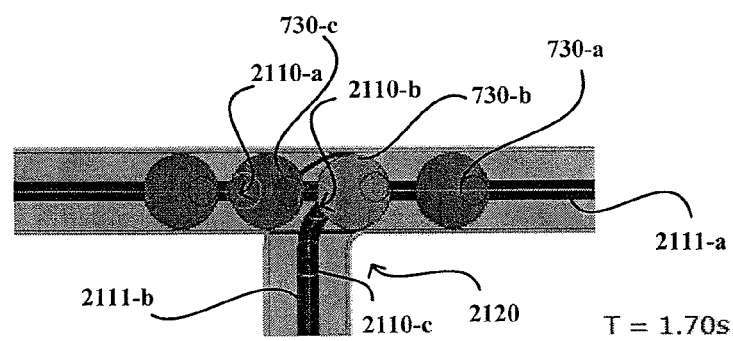

FIG. 10F shows laboratory product transport element 730-*b* now completely on line 2111-*a*, following laboratory product transport element 730-*a*. Note that there may be a bigger distance between laboratory product transport element 730-*b* and laboratory product transport element 730-*a* than there is between laboratory product transport element 730-*b* and laboratory product transport element 730-*c* due to this merging procedure.

FIGS. 11A-11E show another example of throughput control at intersections in accordance with various embodiments. This example may be referred to as a diversion-merge, or pull-off, example. A pull-off example may require a stop position between a diversion area and a merge area to achieve the highest throughput.

Figure 11A:
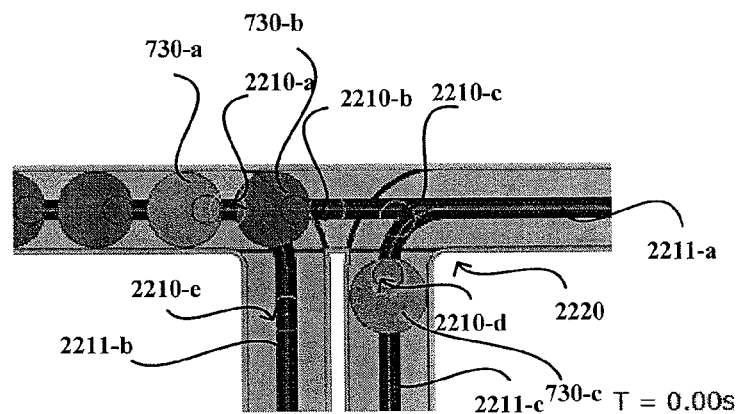
FIG. 11A-11E show another example of throughput control at an intersection, a pull-off example in this case, in accordance with various embodiments.

In FIG. 11A, laboratory product transport element 730-*c* may communicate with near-field communication point 2210-*d*, where it receives a stop signal before it enters merge area 2220. It may receive this stop signal because laboratory product transport element 730-*b* is on its way to the merge area. In another case, laboratory product transport element 730-*c* could get clearance to proceed, in which case laboratory product transport element 730-*b* may be forced to stop at near-field communication device 2210-*b* and stop the queue of other laboratory product transport elements behind it. As there may be a leaving laboratory product transport element 730-*a* behind laboratory product transport element 730-*b*, the better decision may be to let the laboratory product transport element 730-*b* proceed and use the gap from the leaving laboratory product transport element 730-*a* for the merging laboratory product transport element 730-*c*.

Figure 11B:
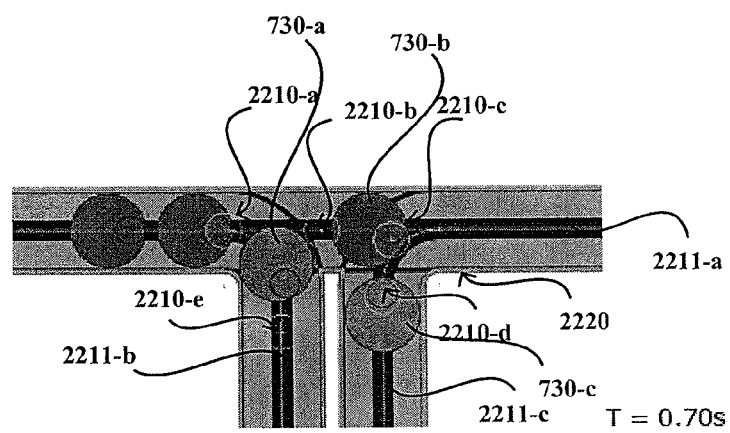
Figure 11C:
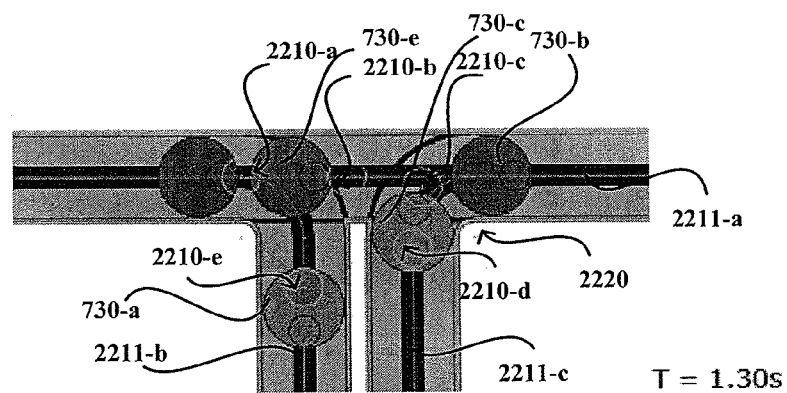

In FIG. 11B, laboratory product transport element 730-*b* can confirm its exit from the merge area 2220 by communicating with near-field communication device 2120-*c*. At this point, near-field communication device 2210-*d* may communicate with laboratory product transport element 730-*c*, giving it clearance to proceed. FIG. 1 IC shows laboratory product transport element 730-*c* beginning to communicate with near-field communication device 2210-*c*, giving an exit confirmation. As a result, they may be no need to send a stop signal to laboratory product transport element 730-*e* as its collision sensors would communicate the need to decelerate.

Figure 11D:
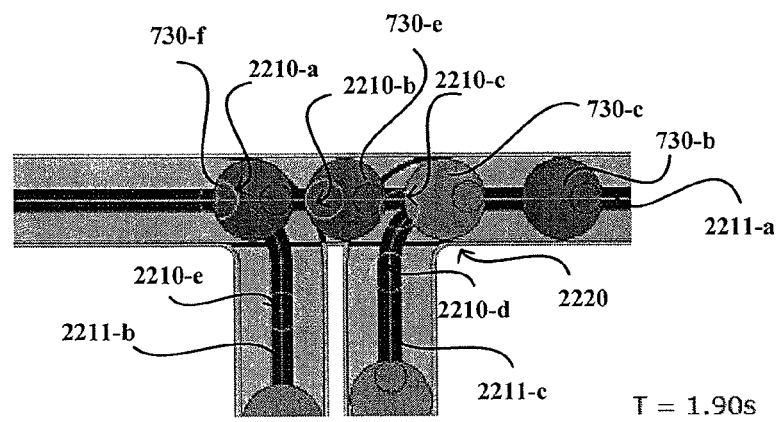
Figure 11E:
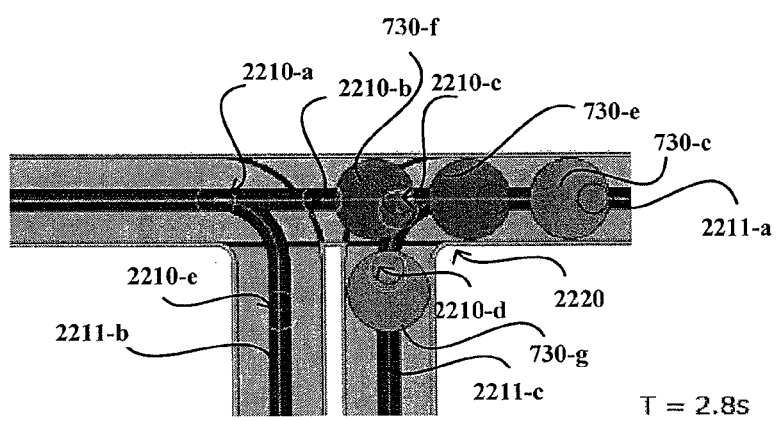

FIG. 11D shows merging laboratory product transport element 730-*c* slipping into the gap between laboratory product transport elements 730-*b* and 730-*e*. FIG. 11E then shows the next merging laboratory product transport element 730-*g* getting clearance to proceed as laboratory product transport element 730-*f* communicates its exit to near-field communication device 2210-*c*.

Figure 12A:
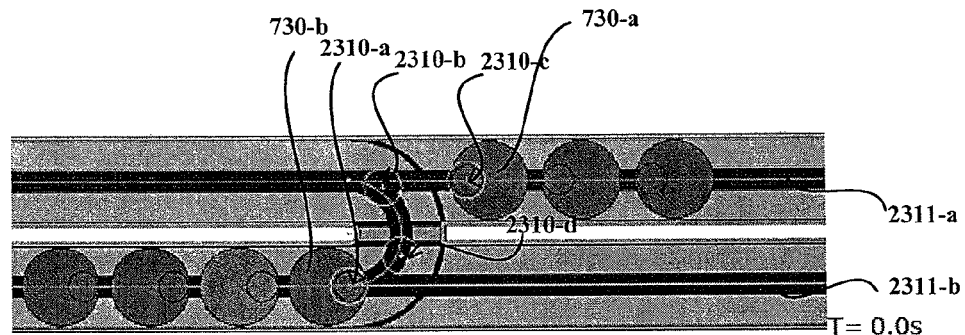
FIGS. 12A-12F show another example of throughput control at an intersection, a short cut example in this case, in accordance with various embodiments.
Figure 12B:
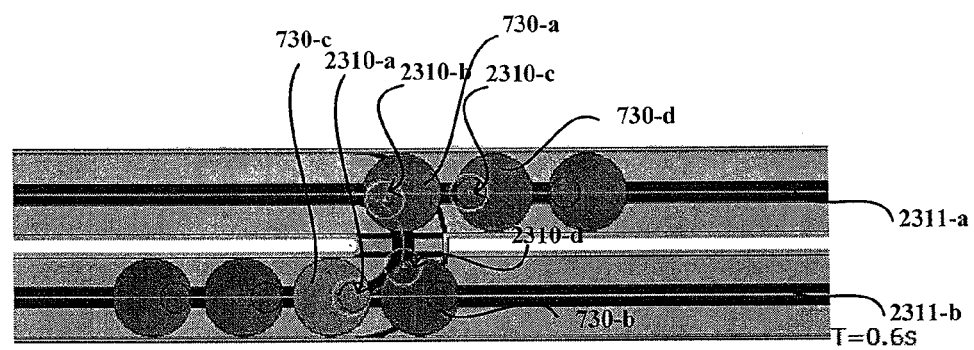
Figure 12C:
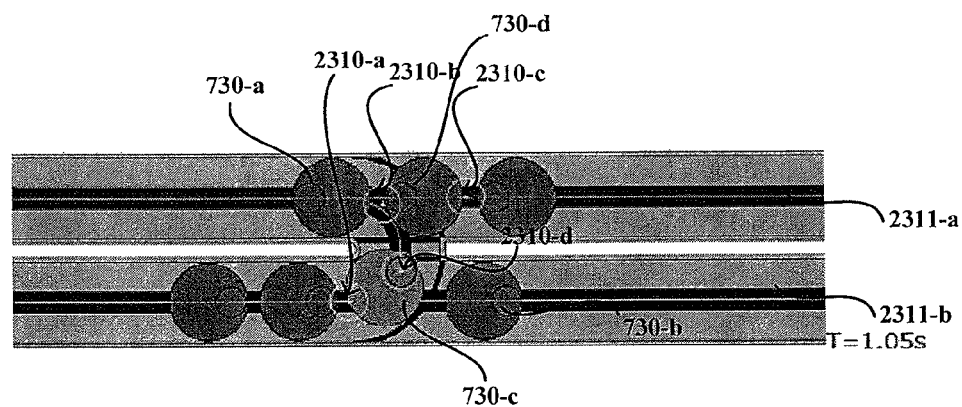

FIGS. 12A-12F show another example of throughput control at intersections in accordance with various embodiments. This example may be referred to as a shortcut example. In FIG. 23A, laboratory product transport element 730-*a* is traveling along line 2311-*a* and communicates with near-field communication device 2310-*c*, receiving a clearance signal. Laboratory product transport element 730-*b* is following line 2311-*b* and just proceeds straight on, receiving a signal from near-field communication device 2310-*a*. In FIG. 12B, laboratory product transport element 730-*c* reaches near-field communication device 2310-*a*. Traffic control may need to decide which lane or line of laboratory product transport elements should get priority. In this example, the laboratory product transport elements 730 following line 2311-*a* have been given higher priority, which means the impact to the throughput on line 2311-*a* can be lower than line 2311-*b*, and may be as low as possible. Laboratory product transport element 730-*d* on line 2311-*a* may receive a clearance signal from near-field communication device 2310-*c*. If the lower lane along line 2311-*b* had been given priority, laboratory product transport element 730-*d* could have been given a stop signal. FIG. 12C shows laboratory product transport element 730-*c* as it attempts to merge onto line 2311-*a*. It is communicating with near-field communication point 2310-*d*, where it may receive a stop signal to allow laboratory product transport elements 730 along line 2311-*a* to proceed because of their higher priority.

Figure 12D:
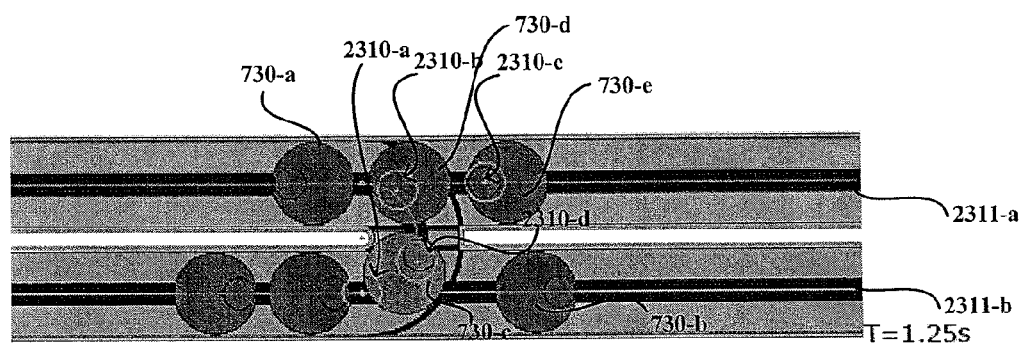
Figure 12E:
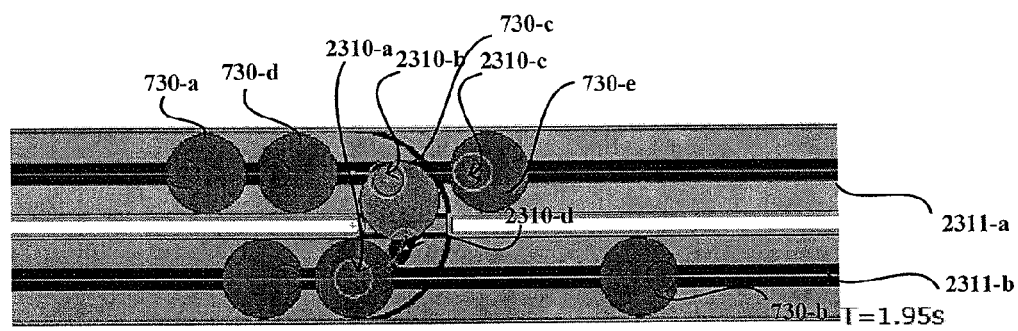

FIG. 12D shows laboratory product transport element 730-*c* receiving a clearance signal from near-field communication device 2310-*d* as laboratory product transport element 730-*d* passes over near-field communication device 2310-*b*, confirming its exit. Laboratory product transport element 730-*e* may be stopped at near-field communication device 2310-*c*. FIG. 12E shows laboratory product transport element 730-*c* communicating with near-field communication device 2310-*b*, confirming its exit from the merge area. At this point, laboratory product transport element 730-*e* can get clearance and proceeds, utilizing its collision sensors to control its distance between it and other laboratory product transport elements, such as laboratory product transport element 730-*c*.

Figure 12F:
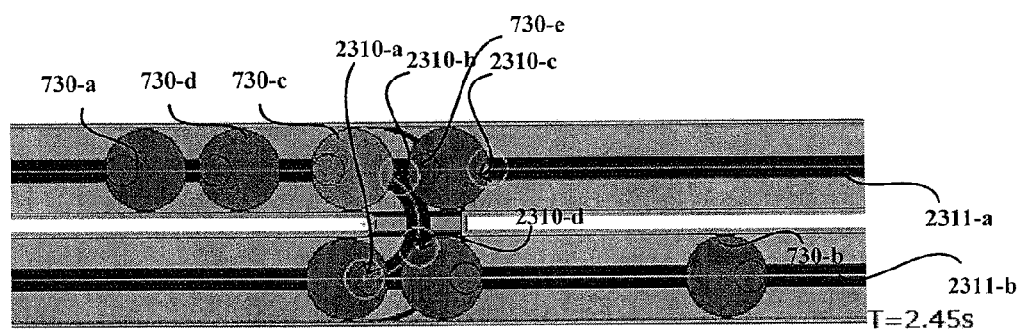

FIG. 12F shows the point where all of the laboratory product transport elements 730 are continuing on the lines 2311 that they are presenting following, and they may reach travel speed again. Depending on the priority, the lane which receives a laboratory product transport element may not lose much throughput, similar to a perpendicular merge. The lane where the turning laboratory product transport element is coming from may lose throughput. For example, in the case of a 1:1 ratio where every second laboratory product transport element 730 takes the shortcut, the remaining throughput of the lower lane may be less than the throughput for the upper lane. A bigger distance between the lanes, such as greater than a laboratory product transport element diameter, may help in some cases. The shortcut could be regarded as two independent intersections, such as a diversion and a merge.

Figures 13A, 13B:
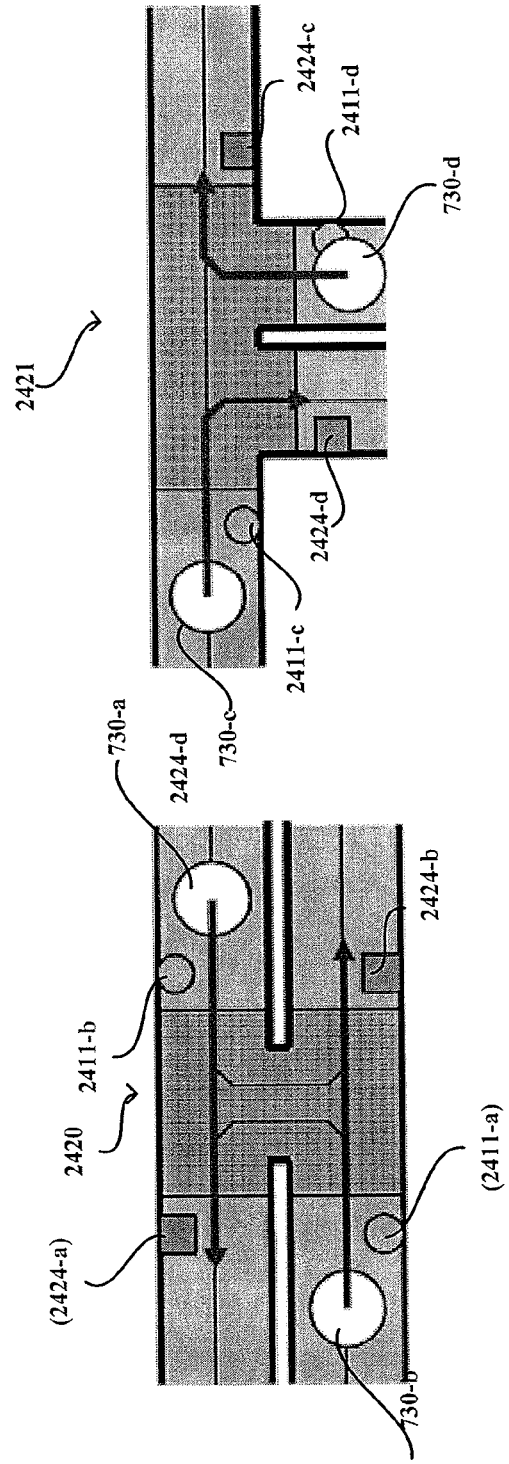
FIGS. 13A and 13B show another example of throughput control at an intersection utilizing RFID tags in accordance with various embodiments.

FIGS. 13A and 13B show two additional examples of throughput control at one or more intersections in accordance with various embodiments. These examples utilize RFID tags 2411 and 2424. Some of these RFID tags, such as 2411, may be positioned before an intersection such as 2420 and 2421; these RFID tags may be referred to as entry RFID tags or enter switch—RFID tags. Some of the RFID tags, such as 2424, may be positioned after an intersection such as 2420 and 2421; these RFID tags may be referred to as exit RFID tags or exit switch-RFID tags. A laboratory product transport element 730 may include an RFID reader that may be able to read the RFID tags positioned before and/or after an intersection and read information from respective RFID tags such as 2411 and/or 2424 to determine a status of a laboratory product transport element's 730 status with respect to the intersection. Throughput control at an intersection may be operated in different ways. In some embodiments, a central controller, such as a line controller, may receive a request for intersection status, such as blocked or free. In some embodiments, local intersection controllers may be utilized that provide signals autonomously when the intersection is blocked or free.

Energy Savings

Some embodiments include methods, systems, and/or devices that may provide energy savings for a laboratory product transport element. Laboratory product transport elements may utilize an energy accumulator, such as a battery or fuel cell. As a result, saving power and therefore a lower charging frequency may be beneficial for different systems. Laboratory product transport elements may utilize information regarding its transportation environment, such as a transfer path arrangement. This information may be utilized in some cases to effectively use power reduction measures.

Embodiments may utilize a variety of techniques to minimize power consumption. In several embodiments, techniques for reducing power consumption may utilize adaptable polling frequency. Depending on the location with a laboratory transport system, such as transfer path arrangement, or other situation in the process, a frequency of a sensor polling can be adapted. The lower the frequency of a sensor polling, the lower the power consumption may be. A variety of different sensors or devices may utilize this adaptable polling frequency approach. For example, collision sensors may utilize adaptable polling frequency. For example, a collision sensor may reduce its polling frequency in a queue of laboratory product transport elements. In some cases, a collision sensor's polling frequency may be adjusted, including reducing its polling frequency, based on its speed, to adapt the frequency to a polling frequency appropriate for the laboratory product transport elements speed. Line following sensors may also utilize adaptable polling frequency methods. In some case, a line following sensor's polling frequency may be adjusted, including reducing its polling frequency, based on its speed, to adapt the frequency to a polling frequency appropriate for the laboratory product transport elements speed. Communication modules may also utilize adaptable polling frequency methods, based on the frequency that communication may need to occur. Some laboratory product transport elements may include a holder that may be able to detect the presence of a laboratory product. Adaptable polling frequency methods may be utilized by reducing and/or minimizing the polling frequency when the holder is empty.

Energy saving may also be achieved in some embodiments through the use of selective activation and/or deactivation of electronic components. In certain situations, some components can even be switched off completely. For example, drive device controllers may be selectively activated and/or deactivated when a laboratory product transport element is not moving, as in general, there is may be no need for motion control when a laboratory product transport element stands still. Different sensors may also be selectively activated and/or deactivated. For example, collisions sensors may be deactivated when it may not be necessary for the collision sensor to detect other laboratory product transport elements. This may occur for example when the laboratory product transport element is located in different locations, such as a processing station or when it is stationary in a queue. A collision sensor may then be selectively activated when it may be needed again, for example, when the laboratory product transport element begins moving again or leaves a particular portion of a transfer path arrangement. Similarly, line following sensors may be selectively activated and/or deactivated. Communication units may also be selectively activated and/or deactivated in order to save energy. For example, when a laboratory product transport element is in a waiting queue, the communication unit can be switched off until the laboratory product transport element moves on. Other sensors, units, and/or aspects of a laboratory product transport element may utilize selective activation and/or deactivation that may help reduce energy consumption.

Energy saving may also be achieved through movement and/or motion control of a laboratory product transport element. For example, drive devices may be operated at different speeds in order reduce energy consumption. Smooth acceleration of a laboratory product transport element in waiting queues may aid in reducing energy consumption. A laboratory product transport element with reduced velocity when entering a track segment with a known queue may also provide energy savings. In some cases, high speeds may be used only where there is a certain probability to keep the high speed for a certain time in order to reduce power consumption. Other movement and/or motion control of a laboratory product transport element may achieve energy savings.

Sample Quality Protection

Some embodiments provide methods, systems, and/or devices for sample quality protection. For example, samples on automated systems can have many different statuses including, but not limited to: open (de-capped)/closed (capped); liquid fill level differs from tube to tube; different type of material like serum, plasma, urines, etc.; tubes with gel or without gel; and/or platelet poor plasma/platelet free plasma. Some of these samples may require a certain care at transportation to avoid remixing, spilling or other loss of quality, while other samples may not require careful transportation. As a general rule it can be said, the less movement, the better for the sample quality. Some embodiments provide a possibility to adapt the individual transport parameters (e.g. velocity, acceleration, and deceleration) to the individual needs of every single sample.

Some embodiments may include moving parameters for different laboratory product transport elements, such as element 30 and/or element 730. Some embodiments may include combinations of movement parameters.

In some embodiments, movement parameters may be stored in a laboratory product transport element. When a laboratory product 50 is put into a holder of a laboratory product transport element 730, a central control can transfer the properties of the laboratory product 50 to the laboratory product transport element 730. The laboratory product transport element 730 itself can determine the appropriate movement parameters out of a internally stored list and performs the movement autonomously. The laboratory product transport element 730 may be aware of the physical layout and the topology of the transfer path arrangement or laboratory transport system and may have a sufficient memory size and CPU performance to perform the movement parameters.

In some embodiments, movement parameters may be updated at different locations or nodes within the transfer path arrangement. This technology may involve both a fast communication with very little latency and a sufficient calculation performance of a central controller. This approach may provide advantages in that it is possible to react to the actual track situation and adjust the parameters accordingly. For example, it may not make sense to accelerate to an enormous high velocity when there is a queue in front of the next node. In combination with a powerful scheduler, this option can provide the smoothest possible control.

Some embodiments may utilize a combination of stored movement parameters on the laboratory product transport element along with receiving movement parameters as the laboratory product transport element moves around a transfer path arrangement. For example, some embodiments may include one or more tables of movement parameters that may be stored in a memory unit in the laboratory product transport element. An example of a table is in Table 1 below. The laboratory product transport element may get the number or ID of the movement parameters to be use at different locations or nodes in a transfer path arrangement; the number or ID may be selected by a central controller. The memory unit in the laboratory product transport element can have code, executable by the control unit to implement a method including causing the laboratory product transport element to travel in a path on a transport path arrangement, wherein the path has a plurality of nodes associated with the path, and wherein the laboratory product transport element moves according to the movement profiles and movement parameters associated with the nodes. Embodiments of the invention can provide advantages such as lower data transfer but still with the option to select the parameters according to the track situation.

TABLE 1

| ID | Predefined Movement Profile | Movement Parameter | Node | Sample Status |
|---|---|---|---|---|
| 001 | Straight path | maintain standard velocity | A | Has sample |
| 002 | 90 degree bend | decelerate | B | Has sample |
| 003 | Right curve | decelerate | C | Has sample |
| 004 | Straight path | accelerate | D | Has sample |
| 005 | Straight path | Accelerate to maximum velocity | E | No sample |
| 006 | Left turn | Move at maximum velocity | F | No sample |

Table 1 above shows some examples of predefined movement profiles and movement parameters that can be associated with different nodes at different points in a transfer path arrangement. Embodiments of the invention are not limited to these specific movement profiles or movement parameters.

As noted in Table 1 above, the velocity of the laboratory product transport element may vary depending upon a number of factors including the geometry of the track. The velocity (or other control parameter) may also depend on the type of sample in a laboratory product or the presence of the sample in the laboratory product. For instance, if the sample has been centrifuged, then the laboratory product transport element may move slowly to avoid upsetting the separation of components in the laboratory product. If the sample is not present, then the laboratory product transport element may be programmed to move quickly to improve throughput.

Embodiments may provide different advantages by providing individual movement parameters, such as velocity information, for specific laboratory product transport elements that may be carrying specific laboratory products. For example, an empty laboratory product transport element or laboratory product transport elements with empty laboratory products can move with maximum velocities, acceleration, and/or deceleration. Movement parameters may help reduce the necessary number of laboratory product transport elements since unproductive, empty-time can be minimized.

In some cases, adaptable velocity parameters can provide the possibility to move fast on straight sections and decelerate in front of a bend. This may allow for high speed track sections and/or velocity parameters that are not limited by bend radiuses. In some cases, in cumulating queues, acceleration and/or deceleration can be reduced to a minimum. This may provide for sample care along with minimizing power consumption.

In some cases, battery status may also influence the movement parameters. For example, in case the battery or energy accumulator in general is low, the velocity, acceleration, and/or deceleration can be reduced to save energy. In this case, laboratory product transport element energy starvation becomes very unlikely.

Figure 14:
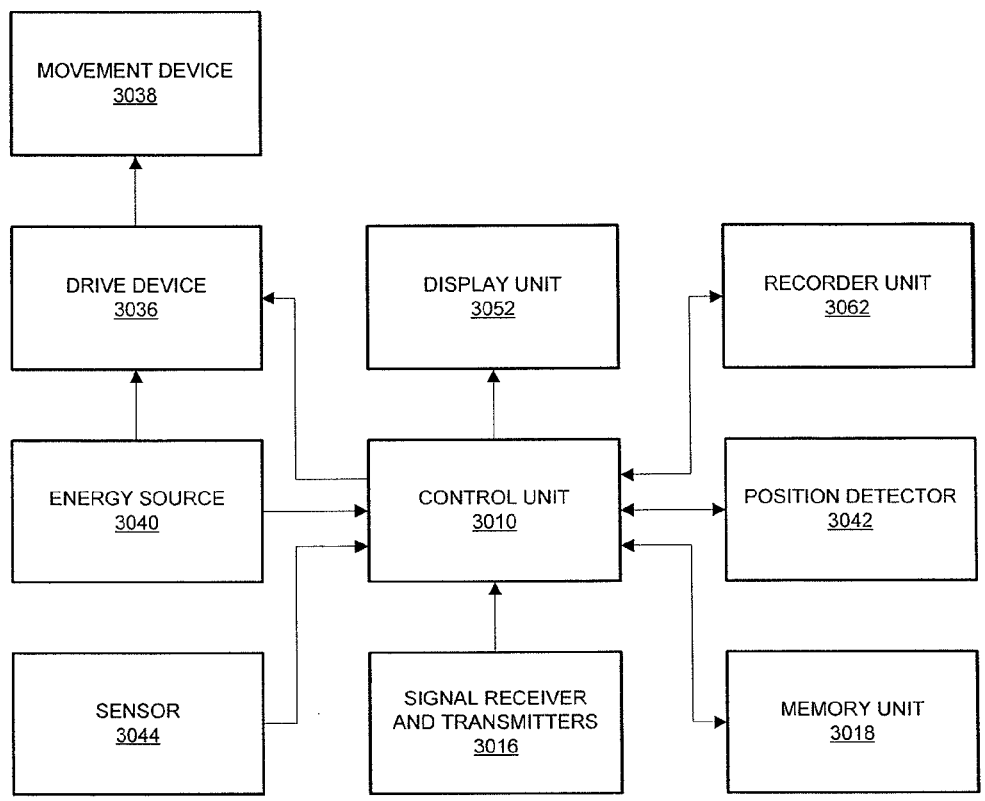
FIG. 14 shows a block diagram showing elements of a laboratory product transport element.

FIG. 14 shows a block diagram of some components in a laboratory product transport element according to an embodiment of the invention. Many of the components in FIG. 14 are already described in detail above, and the descriptions above are herein incorporated by references. FIG. 14 shows a central control unit 3010, which may be in the form of one or more processors such as one or more microprocessors. A memory unit 3018 may be coupled to the control unit 3010. The memory unit 3018 may comprise and store code, executable by the processor in the control unit 3010 to perform any of the above described functions described above, including but not limited to fine positioning, lift-off protection, self-diagnosis, collision avoidance, etc.

An energy source 3040 (e.g., an energy accumulator and/or an energy receiver) may provide power to a drive device 3036 (e.g., a motor), which may be coupled to a movement device 3038 (e.g., a wheel). As shown and as described above, a position detector 3042, a display unit 3052 and a recorder unit 3062 may also be operatively coupled (e.g., electrically coupled) to the control unit 3010.

In order to communicate with its external environment, one or more sensors 3044 may be operatively coupled to the control unit 3010, and one or more signal receivers and transmitters 3106 can be coupled to the control unit 3010. The sensors 3044 may communicate with devices such as near field communication devices on a transfer path. The signal receiver(s) 3016 receive control and/or drive signals for the laboratory product transport element from a host control system. The signal transmitters 3016 can transmit signals to the host control system regarding its status (e.g., its internal status, its status with respect to other laboratory product transport elements, etc.).

Figure 15:
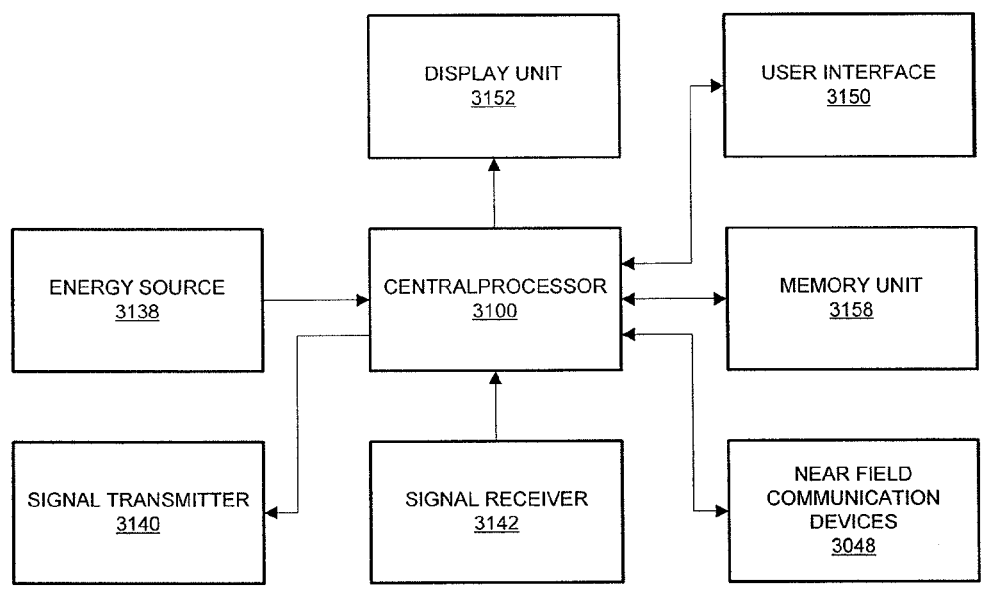
FIG. 15 shows a block diagram of a system for controlling a laboratory product.

FIG. 15 shows a block diagram illustrating some components of a host control system according to an embodiment of the invention. Many of the components in FIG. 15 are already described in detail above, and the descriptions above are herein incorporated by references. It may include a central processor 3100, which can be powered by an energy source 3138. A display unit 3152 and a user interface 3150 may be coupled to the control processor 3100 to provide information and control to a user of the host control system. A memory unit 3158 may be coupled to the central processor 3100 and it may store code for causing the central processor 3100 to perform any of the functions described above for controlling or managing the movement of the various laboratory product transport elements described above including collision avoidance, traffic control, status, etc.

To communicate with the laboratory product transport elements, a signal transmitter 3140 for transmitting control signals to the laboratory transport product elements, a signal receiver 3142 for receiving signals from the laboratory product transport elements, and near field communication devices 3048 may be controlled by and in operative communication with the central processor 3100.

The previous description provides exemplary embodiments only, and is not intended to limit the scope, applicability, or configuration of the disclosure. Rather, the previous description of the exemplary embodiments will provide those skilled in the art with an enabling description for implementing one or more exemplary embodiments. It is understood that various changes may be made in the function and arrangement of elements without departing from the spirit and scope of the invention. Several embodiments were described herein, and while various features are ascribed to different embodiments, it should be appreciated that the features described with respect to one embodiment may be incorporated within other embodiments as well. By the same token, however, no single feature or features of any described embodiment should be considered essential to every embodiment of the invention, as other embodiments of the invention may omit such features.

Specific details are given in the previous description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have also included additional steps or operations not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Furthermore, embodiments may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

While detailed descriptions of one or more embodiments have been give above, various alternatives, modifications, and equivalents will be apparent to those skilled in the art without varying from the spirit of the invention. Moreover, except where clearly inappropriate or otherwise expressly noted, it should be assumed that the features, devices, and/or components of different embodiments may be substituted and/or combined. Thus, the above description should not be taken as limiting the scope of the invention. Lastly, one or more elements of one or more embodiments may be combined with one or more elements of one or more other embodiments without departing from the scope if the invention.

What is claimed is:

1. A laboratory product transport element comprising:
   an energy source configured to furnish drive power;
   at least one signal receiver configured to receive control signals;
   a control unit configured to generate drive signals as a function of at least one control signal obtained from the at least one signal receiver;
   at least one movement device, with which the laboratory product transport element can move independently on a transfer path;
   at least one drive device configured to drive the at least one movement device as a function of the drive signals of the control unit, the at least one drive device being driven by the drive power; and
   at least one holder to hold a laboratory product to be transported;
   the laboratory product transport element further comprising an external communication interface, an output device, and a memory unit coupled to the control unit, wherein the memory unit comprises code executable by the control unit to implement a method comprising generating an error signal if the laboratory product is improperly removed from the at least one holder, wherein the error signal is a first error signal and wherein the method further comprises:
   generating a second error signal when the laboratory product transport element is improperly removed from a predefined path that the laboratory product transport element is intended to follow.

2. The laboratory product transport element of claim 1 wherein the method further comprises:
   detecting the improper removal of the laboratory product with an optical sensor.

3. The laboratory product transport element of claim 1 wherein the method further comprises:
   detecting the improper removal of the laboratory product with a mechanical sensor.

4. The laboratory product transport element of claim 1 wherein the method further comprises:

detecting the improper removal of the laboratory product with a radio-frequency identification (RFID) tag coupled with the laboratory product.

5. The laboratory product transport element of claim 1 wherein the method further comprises:
detecting the improper removal of the laboratory product transport element with a line following sensor coupled with the laboratory product transport element.

6. A method of controlling a laboratory product transport element according to claim 1, wherein the method comprises:
generating the error signal if the laboratory product is improperly removed from the at least one holder.

7. The method according to claim 6, wherein improper removal of the laboratory product from the at least one holder is detected by means of an optical sensor, a mechanical sensor, a radio-frequency identification (RFID) tag coupled with the laboratory product, a line following sensor coupled with the laboratory product transport element, a drive signal or using a central control.

8. The method according to claim 6 wherein the error signal is a first error signal and wherein the method further comprises:
generating a second error signal when the laboratory product transport element is improperly removed from a predefined path that the laboratory product transport element is intended to follow.

9. The method according to claim 8 wherein the method further comprises:
directing the laboratory product transport element to a specific location after generating the second error signal.

10. A laboratory product transport element comprising:
an energy source configured to furnish drive power;
at least one signal receiver configured to receive control signals;
a control unit configured to generate drive signals as a function of at least one control signal obtained from the at least one signal receiver;
at least one movement device, with which the laboratory product transport element can move independently on a transfer path;
at least one drive device configured to drive the at least one movement device as a function of the drive signals of the control unit, the at least one drive device being driven by the drive power; and
at least one holder to hold a laboratory product to be transported;
the laboratory product transport element further comprising an external communication interface, an output device, and a memory unit coupled to the control unit, wherein the memory unit comprises code executable by the control unit to implement a method comprising generating an error signal if the laboratory product is improperly removed from the at least one holder, and wherein the method further comprises:
detecting the improper removal of the laboratory product transport element with a drive signal.

11. The laboratory product transport element of claim 1 wherein the method further comprises:
detecting the improper removal of the laboratory product transport element using a central control.

12. The laboratory product transport element of claim 1 wherein the method further comprises:
sending a signal reporting the one or more errors signals.

13. A laboratory product transport element comprising:
an energy source configured to furnish drive power;
at least one signal receiver configured to receive control signals;
a control unit configured to generate drive signals as a function of at least one control signal obtained from the at least one signal receiver;
at least one movement device, with which the laboratory product transport element can move independently on a transfer path;
at least one drive device configured to drive the at least one movement device as a function of the drive signals of the control unit, the at least one drive device being driven by the drive power; and
at least one holder to hold a laboratory product to be transported;
the laboratory product transport element further comprising an external communication interface, an output device, and a memory unit coupled to the control unit, wherein the memory unit comprises code executable by the control unit to implement a method comprising generating an error signal if the laboratory product is improperly removed from the at least one holder, and wherein the method further comprises:
generating one or more verification signals, wherein the verification signal reflects a successful sample product load, a successful sample product unload, or a successful sample product decapping.

14. A laboratory product transport element comprising:
an energy source configured to furnish drive power;
at least one signal receiver configured to receive control signals;
a control unit configured to generate drive signals as a function of at least one control signal obtained from the at least one signal receiver;
at least one movement device, with which the laboratory product transport element can move independently on a transfer path;
at least one drive device configured to drive the at least one movement device as a function of the drive signals of the control unit, the at least one drive device being driven by the drive power; and
at least one holder to hold a laboratory product to be transported;
the laboratory product transport element further comprising an external communication interface, an output device, and a memory unit coupled to the control unit, wherein the memory unit comprises code executable by the control unit to implement a method comprising generating an error signal if the laboratory product is improperly removed from the at least one holder, wherein the method further comprises:
directing the laboratory product transport element to a specific location after generating the error signal.

* * * * *

UNITED STATES PATENT AND TRADEMARK OFFICE
CERTIFICATE OF CORRECTION

PATENT NO.        : 9,459,273 B2
APPLICATION NO.   : 14/117573
DATED             : October 4, 2016
INVENTOR(S)       : Michael Eberhardt et al.

Page 1 of 1

It is certified that error appears in the above-identified patent and that said Letters Patent is hereby corrected as shown below:

On the Title Page

Item (75) "Inventors", please update the Inventor order to the following:

Michael Eberhardt, Munich, (DE);
Martin Mueller, Schliersee-Neuhaus, (DE);
Sebastian Wiessner, Stephanskirchen, (DE);
Thomas Moix, Lausanne, (CH);
Guillaume Ding, Fribourg, (CH);
Jurjen Zoethout, La Sarraz, (CH)

Signed and Sealed this
Ninth Day of May, 2017

Michelle K. Lee
*Director of the United States Patent and Trademark Office*